(12) United States Patent
Sams et al.

(10) Patent No.: US 7,674,912 B2
(45) Date of Patent: Mar. 9, 2010

(54) PRO-DRUGS OF N-THIAZOL-2-YL-BENZAMIDE DERIVATIVES

(75) Inventors: Anette Graven Sams, Vaerloese (DK); Benny Bang-Andersen, Copenhagen S. (DK); Gitte Mikkelsen, Ballerup (DK); Mogens Larsen, Smoerum (DK)

(73) Assignee: H. Lundbeck A/S, Valby, Copenhagen (DK)

( * ) Notice: Subject to any disclaimer, the term of this patent is extended or adjusted under 35 U.S.C. 154(b) by 104 days.

(21) Appl. No.: 11/409,884

(22) Filed: Apr. 24, 2006

(65) Prior Publication Data

US 2006/0264485 A1 Nov. 23, 2006

Related U.S. Application Data

(60) Provisional application No. 60/675,029, filed on Apr. 26, 2005, provisional application No. 60/720,963, filed on Sep. 26, 2005, provisional application No. 60/743,865, filed on Mar. 28, 2006.

(30) Foreign Application Priority Data

Apr. 25, 2005 (DK) ............................... 2005 00594

(51) Int. Cl.
*A61K 31/426* (2006.01)
*C07F 9/09* (2006.01)
*A61K 33/42* (2006.01)
*C07D 277/46* (2006.01)

(52) U.S. Cl. .................. 548/195; 548/112; 514/92; 514/371

(58) Field of Classification Search .................. 548/195
See application file for complete search history.

(56) References Cited

U.S. PATENT DOCUMENTS

| | | | |
|---|---|---|---|
| 5,344,736 A | | 9/1994 | Komiyama et al. |
| 6,140,330 A | * | 10/2000 | Mori et al. .............. 514/254.03 |
| 6,727,269 B1 | * | 4/2004 | Moinet et al. ................ 514/370 |
| 2004/0053982 A1 | | 3/2004 | Press et al. |
| 2004/0138235 A1 | | 7/2004 | Grzelak et al. |
| 2004/0235888 A1 | | 11/2004 | Yamamori |
| 2006/0154974 A1 | | 7/2006 | Sams et al. |
| 2007/0105919 A1 | | 5/2007 | Nakajima et al. |

FOREIGN PATENT DOCUMENTS

| | | |
|---|---|---|
| DE | 855120 C | 1/1953 |
| DE | 855120 C | 1/1953 |
| EP | 0407200 A1 | 1/1991 |
| EP | 870765 A1 | 10/1998 |
| EP | 0934938 A | 8/1999 |
| EP | 1176139 A1 | 1/2002 |
| EP | 1295872 A1 | 3/2003 |
| EP | 1354880 A | 10/2003 |
| WO | WO 96/36619 A1 | 11/1996 |
| WO | WO 99/64418 | 12/1999 |
| WO | WO 00/26202 A | 5/2000 |
| WO | WO 00/53573 A1 | 9/2000 |
| WO | WO 00/62778 A1 | 10/2000 |
| WO | WO 01/94309 A1 | 12/2001 |
| WO | WO 02/42298 | 5/2002 |
| WO | WO 02/055083 A1 | 7/2002 |
| WO | WO 03/045386 A | 6/2003 |
| WO | WO 03/053946 A | 7/2003 |
| WO | WO 2004/085388 A2 | 10/2004 |
| WO | WO 2005/003779 A | 4/2005 |
| WO | WO 2005/037779 A | 4/2005 |
| WO | WO 2005/003972 | 5/2005 |
| WO | WO 2005/039572 A | 5/2005 |
| WO | WO 2005/094376 A2 | 10/2005 |
| WO | WO 2006/028958 A2 | 3/2006 |
| WO | WO 2006/032273 A1 | 3/2006 |
| WO | WO 2006/051704 A | 5/2006 |
| WO | WO 2007/015528 A1 | 2/2007 |
| WO | WO2007/022415 A2 | 2/2007 |

OTHER PUBLICATIONS

Guttman et al., Canadian Medical Association Journal, Feb. 4, 2003, 168(3), pp. 293-301.*
Thomas et al., Human Molecular Genetics, 2007, vol. 16, Review Issue 2, pp. R183-R194.*
Blum, D., et al. A Dual Role of Adenosine A 2A Receptors in 3-Nitropropionic Acid-Induced Striatal Lesions: Implications for the Neuroprotective Potential of A 2A Antagonists, J. Neurosci. Jun. 15, 2003, 23(12):5361-5369.
Bundgaard, Hans, ed. Design of Prodrugs Elsevier Science Publishing Company (Amsterdam, The Netherlands). 1985. Chapter 1 (Bundgaard, H.), Section 1.2, pp. 3-10 and Section 1.3, pp. 10-27; Chapter 2 (Banerjee, P.K. and Amidon, G.L.), Section 2.5, pp. 105-118 and Section 2.6, pp. 118-121.
Dall'Igna, O.P., et al. Neuroprotection by caffeine and adenosine A 2A receptor blockade of β-amyloid neurotoxicity, Br. J. Pharmacol. 2003, 138:1207-1209.
El Yacoubi, M., et al. Adenosine A 2A receptor antagonists are potential antidepressants: evidence based on pharmacology and A 2A receptor knockout mice. Br. J. Pharmacol. 2001. 134:68-77.
Ettmayer, P., et al. Lessons learned from marketed and investigational prodrugs. J. Med. Chem. May 6, 2004. 47(10)2393-2404.
Ikeda, K., et al. Neuroprotection by adenosine A 2A receptor blockade in experimental models of Parkinson's disease. J. Neurochem. 2002. 80:262-270.
Impagnatiello, F., et al. Adenosine receptors in neurological disorders. Emerging Therapeutic Targets. 2000. 4(5):635-664.

(Continued)

*Primary Examiner*—Laura L. Stockton
(74) *Attorney, Agent, or Firm*—Stephen G. Kalinchak; Margaret M. Buck; Mary C. Johnson

(57) ABSTRACT

The invention relates to compounds of the formula I

A-B-Z          I wherein the variables are as defined in the claims. The compounds are pro-drugs of $A_{2A}$-receptor ligands with improved aqueous solubility, and are useful in the treatment of neurological and psychiatric disorders where an $A_{2A}$-receptor is implicated.

23 Claims, No Drawings

OTHER PUBLICATIONS

Krise, J. P., et al. Novel prodrug approach for tertiary amines: Synthesis and preliminary evaluation of N-phosphonooxymethyl prodrugs. J. Med. Chem. 1999. 42(16). 3094-3100.

Methippara, M.M., et al. Effects on sleep of microdialysis of adenosine A1 and A2 receptor analogs into the lateral preoptic area of rats. Am. J. Physiol. Regul. Integr. Comp. Physiol. 2005. 289:R1715-R1723.

Monopoli, A., et al. Blockade of adenosine A 2A receptors by SCH 58261 results in neuroprotective effects in cerebral ischaemia in rats. NeuroRepor. Dec. 1998. 9(17):3955-59.

Nagel, J., et al. Effects of an Adenosine A 2A Receptor Blockade in the Nucleus Accumbens on Locomotion, Feeding, and Prepulse Inhibition in Rats. Synapse. 2003. 49:279-28.

Ongini, E., et al. Adenosine A 2A Receptors and Neuroprotection. Annals of NY Academy of Sciences. 1997. 825(1):30.

Ongini, E., et al. Dual Actions of A 2A Adenosine Receptor Antagonists on Motor Dysfunction and Neurodegenerative Processes. Drug Dev. Res. 2001. 52:379-386.

Prediger, R.D.S., et al. Blockade of adenosine A2A receptors reverses short-term social memory impairments in spontaneously hypertensive rats. Behav. Brain Research. 2005. 159:197-205.

Richardson, P.J., et al. Adenosine A 2A receptor antagonists as new agents for the treatment of Parkinson's disease. TiPS. Sep. 1997. 18:338-344.

Svenningsson, P., et al. Distribution, Biochemistry and Function of Striatal Adenosine A 2A Receptors. Progress in Neurobiology. 1999. 59:355-396.

Gondi, Sudershan R. et al. (2004) Synthetic Communications, vol. 34, No. 17, pp. 3061-3072.

Jacobsen, K.A. and Gao, Z. (2006) Nature Reviews, Drug Discovery, vol. 5, pp. 247-264.

CAS Registry No. 768290-60-4; Oct. 24, 2004; Chemical Library Supplier Vitas-M.
CAS Registry No. 763063-10-1; Oct. 15, 2004.
CAS Registry No. 760925-04-0; Oct. 11, 2004.
CAS Registry No. 757167-34-3; Oct. 6, 2004.
CAS Registry No. 734518-98-0; Aug. 27, 2004.
CAS Registry No. 728930-56-1; Aug. 19, 2004; Chemical Library Supplier Vitas-M.
CAS Registry No. 702647-52-7; Jul. 2, 2004; Chemical Library Supplier ChemBridge Corporation.
CAS Registry No. 693819-92-0; Jun. 16, 2004; Chemical Library Supplier ChemBridge Corporation.
CAS Registry No. 693814-29-8; Jun. 16, 2004; Chemical Library Supplier ChemBridge Corporation.
CAS Registry No. 693808-23-0; Jun. 16, 2004; Chemical Library Supplier ChemBridge Corporation.
CAS Registry No. 693805-33-3; Jun. 16, 2004; Chemical Library Supplier ChemBridge Corporation.
CAS Registry No. 693795-29-8; Jun. 16, 2004; Chemical Library Supplier ChemBridge Corporation.
CAS Registry No. 693265-95-1; Jun. 15, 2004; Chemical Library Supplier ChemBridge Corporation.
CAS Registry No. 693265-12-2; Jun. 15, 2004; Chemical Library Supplier ChemBridge Corporation.
CAS Registry No. 686739-77-5; May 28, 2004; Chemical Library Supplier ChemDiv, Inc.
CAS Registry No. 667410-90-4; Mar. 25, 2004; Chemical Library Supplier Scientific Exchange, Inc.
CAS Registry No. 667410-45-9; Mar. 25, 2004; Chemical Library Supplier Scientific Exchange, Inc.
CAS Registry No. 667403-59-0; Mar. 25, 2004; Chemical Library Supplier Scientific Exchange, Inc.
CAS Registry No. 663185-58-8; Mar. 15, 2004; Chemical Library Supplier ChemBridge Corporation.
CAS Registry No. 663185-33-9; Mar. 15, 2004; Chemical Library Supplier Vitas-M.
CAS Registry No. 547758-27-0; Jul. 14, 2003; Chemical Library Supplier Ambinter.
CAS Registry No. 547758-03-2; Jul. 14, 2003; Chemical Library Supplier Ambinter.
CAS Registry No. 546092-64-2; Jul. 11, 2003; Chemical Library Supplier Ambinter.
CAS Registry No. 545428-66-8; Jul. 10, 2003; Chemical Library Supplier Ambinter.
CAS Registry No. 502170-70-9; Apr. 8, 2003.
CAS Registry No. 500538-95-4; Mar. 25, 2003.
CAS Registry No. 500350-68-5; Mar. 24, 2003; Chemical Library Supplier Ambinter.
CAS Registry No. 500263-48-9; Mar. 23, 2003; Chemical Library Supplier Interchim.
CAS Registry No. 500262-43-1; Mar. 23, 2003; Chemical Library Supplier Interchim.
CAS Registry No. 443748-99-0; Aug. 13, 2002; Chemical Library Supplier Ambinter.
CAS Registry No. 428840-18-0; Jun. 12, 2002; Chemical Library Supplier ChemBridge Corporation.
CAS Registry No. 428503-55-3; Jun. 11, 2002; Chemical Library Supplier ChemBridge Corporation.
CAS Registry No. 405902-02-5; Apr. 18, 2002; Chemical Library Supplier Ambinter.
CAS Registry No. 404898-48-2; Apr. 10, 2002; Chemical Library Supplier Ambinter.
CAS Registry No. 404845-99-4; Apr. 9, 2002; Chemical Library Supplier ChemBridge Corporation.
CAS Registry No. 404832-67-3; Apr. 9, 2002; Chemical Library Supplier ChemBridge Corporation.
CAS Registry No. 404831-52-3; Apr. 9, 2002; Chemical Library Supplier Ambinter.
CAS Registry No. 404593-33-5; Apr. 8, 2002; Chemical Library Supplier Ambinter.
CAS Registry No. 404586-56-7; Apr. 8, 2002; Chemical Library Supplier Scientific Exchange, Inc.
CAS Registry No. 404585-17-7; Apr. 8, 2002; Chemical Library Supplier ChemBridge Corporation.
CAS Registry No. 404584-87-8; Apr. 8, 2002; Chemical Library Supplier Ambinter.
CAS Registry No. 404583-73-9; Apr. 8, 2002; Chemical Library Supplier Interchim.
CAS Registry No. 404378-49-0; Apr. 5, 2002; Chemical Library Supplier Ambinter.
CAS Registry No. 404370-61-2; Apr. 5, 2002; Chemical Library Supplier Ambinter.
CAS Registry No. 404362-66-9; Apr. 5, 2002; Chemical Library Supplier Interchim.
CAS Registry No. 402598-30-5; Mar. 22, 2002; Chemical Library Supplier Scientific Exchange, Inc.
CAS Registry No. 402597-41-5; Mar. 22, 2002; Chemical Library Supplier Ambinter.
CAS Registry No. 402583-28-2; Mar. 22, 2002; Chemical Library Supplier Ambinter.
CAS Registry No. 385388-07-8; Jan. 22, 2002; Chemical Library Supplier Interbioscreen, Ltd.
CAS Registry No. 384369-81-7; Jan. 19, 2002; Chemical Library Supplier Interbioscreen, Ltd.
CAS Registry No. 381707-47-7; Jan. 10, 2002; Chemical Library Supplier Interbioscreen, Ltd.
CAS Registry No. 381705-82-4; Jan. 10, 2002; Chemical Library Supplier Interbioscreen, Ltd.
CAS Registry No. 380578-78-9; Jan. 7, 2002; Chemical Library Supplier Interbioscreen, Ltd.
CAS Registry No. 380563-05-3; Jan. 7, 2002; Chemical Library Supplier Interbioscreen, Ltd.
CAS Registry No. 372953-39-4; Dec. 3, 2001.
CAS Registry No. 371117-55-4; Nov. 20, 2001; Chemical Library Supplier Interbioscreen, Ltd.
CAS Registry No. 364748-43-6; Oct. 26, 2001; Chemical Library Supplier Ambinter.
CAS Registry No. 364748-39-0; Oct. 26, 2001; Chemical Library Supplier Ambinter.
CAS Registry No. 364620-93-9; Oct. 25, 2001; Chemical Library Supplier ChemBridge Corporation.
CAS Registry No. 364619-30-7; Oct. 25, 2001; Chemical Library Supplier Scientific Exchange, Inc.

CAS Registry No. 364599-62-2; Oct. 25, 2001; Chemical Library Supplier Ambinter.
CAS Registry No. 355403-34-8; Sep. 10, 2001; Chemical Library Supplier ChemStar, Ltd.
CAS Registry No. 354121-19-0; Aug. 31, 2001; Chemical Library Supplier Scientific Exchange, Inc.
CAS Registry No. 351988-92-6; Aug. 20, 2001; Chemical Library Supplier Scientific Exchange, Inc.
CAS Registry No. 351498-95-8; Aug. 16, 2001; Chemical Library Supplier Scientific Exchange, Inc.
CAS Registry No. 349623-95-6; Aug. 1, 2001; Chemical Library Supplier Microchemistry Ltd.
CAS Registry No. 339207-36-2; Jun. 1, 2001; Chemical Library Supplier Zelinsky Institute of Organic Chemistry.
CAS Registry No. 333438-99-6; Apr. 30, 2001; Chemical Library Supplier AsInEx.
CAS Registry No. 333435-53-3; Apr. 30, 2001; Chemical Library Supplier AsInEx.
CAS Registry No. 333343-28-5; Apr. 27, 2001; Chemical Library Supplier Scientific Exchange, Inc.
CAS Registry No. 333343-27-4; Apr. 27, 2001; Chemical Library Supplier Scientific Exchange, Inc.
CAS Registry No. 332033-29-1; Apr. 23, 2001; Chemical Library Supplier AsInEx.
CAS Registry No. 330831-74-8; Apr. 11, 2001; Chemical Library Supplier Scientific Exchange, Inc.
CAS Registry No. 330828-15-4; Apr. 11, 2001; Chemical Library Supplier Ambinter.
CAS Registry No. 330634-85-0; Apr. 10, 2001; Chemical Library Supplier ChemDiv, Inc.
CAS Registry No. 312595-57-6; Jan. 3, 2001; Chemical Library Supplier ChemDiv, Inc.
CAS Registry No. 312595-53-2; Jan. 3, 2001; Chemical Library Supplier AsInEx.
CAS Registry No. 312533-59-8; Jan. 2, 2001; Chemical Library Supplier Scientific Exchange, Inc.
CAS Registry No. 312518-75-5; Jan. 2, 2001; Chemical Library Supplier Chemical Block Ltd.
CAS Registry No. 311314-47-3; Dec. 27, 2000; Chemical Library Supplier ChemDiv, Inc.
CAS Registry No. 309283-62-3; Dec. 18, 2000; Chemical Library Supplier ChemDiv, Inc.
CAS Registry No. 305358-93-4; Nov. 30, 2000; Chemical Library Supplier Scientific Exchange, Inc.
CAS Registry No. 305358-92-3; Nov. 30, 2000; Chemical Library Supplier Scientific Exchange, Inc.
CAS Registry No. 305358-91-2; Nov. 30, 2000; Chemical Library Supplier Scientific Exchange, Inc.
CAS Registry No. 305358-90-1; Nov. 30, 2000; Chemical Library Supplier Scientific Exchange, Inc.
CAS Registry No. 305358-09-2; Nov. 30, 2000; Chemical Library Supplier Scientific Exchange, Inc.
CAS Registry No. 304507-98-0; Nov. 27, 2000; Chemical Library Supplier AsInEx.
CAS Registry No. 302958-93-6; Nov. 15, 2000.
CAS Registry No. 302958-46-9; Nov. 15, 2000.
CAS Registry No. 302927-86-2; Nov. 15, 2000; Chemical Library Supplier AsInEx.
CAS Registry No. 294891-94-4; Oct. 12, 2000; Chemical Library Supplier AsInEx.
CAS Registry No. 294891-92-2; Oct. 12, 2000; Chemical Library Supplier AsInEx.
CAS Registry No. 294890-49-6; Oct. 12, 2000; Chemical Library Supplier ChemDiv, Inc.
CAS Registry No. 292072-63-0; Oct. 2, 2000.
CAS Registry No. 292071-57-9; Oct. 2, 2000; Chemical Library Supplier Scientific Exchange, Inc.
CAS Registry No. 292070-16-7; Oct. 2, 2000.
CAS Registry No. 271773-11-6; Jun. 21, 2000.
CAS Registry No. 267657-40-9; Jun. 1, 2000.
CAS Registry No. 267657-39-6; Jun. 1, 2000.
CAS Registry No. 267657-38-5; Jun. 1, 2000.
CAS Registry No. 267656-13-3; Jun. 1, 2000.
CAS Registry No. 267656-12-2; Jun. 1, 2000.
CAS Registry No. 267656-11-1; Jun. 1, 2000.
CAS Registry No. 267656-07-05; Jun. 1, 2000.
CAS Registry No. 206881-97-2; Jun. 11, 1998.
CAS Registry No. 206881-93-8; Jun. 11, 1998.
CAS Registry No. 185105-91-3; Jun. 17, 1997.
CAS Registry No. 185105-81-1; Jan. 16, 1997.
CAS Registry No. 185105-80-0; Jan. 16, 1997.
CAS Registry No. 185105-62-8; Jan. 16, 1997.
CAS Registry No. 185105-61-7; Jan. 16, 1997.
CAS Registry No. 185105-58-2; Jan. 16, 1997.
CAS Registry No. 185105-57-1; Jan. 16, 1997.
CAS Registry No. 185105-56-0; Jan. 16, 1997.
CAS Registry No. 185105-44-6; Jan. 16, 1997.
CAS Registry No. 185105-40-2; Jan. 16, 1997.
CAS Registry No. 185105-31-1; Jan. 16, 1997.
CAS Registry No. 185105-30-0; Jan. 16, 1997.
CAS Registry No. 143886-38-8; Oct. 9, 1992.
CAS Registry No. 134502-79-7; Jun. 28, 1991.
CAS Registry No. 100395-15-1; Feb. 22, 1986.
CAS Registry No. 99989-49-8; Feb. 1, 1986.
CAS Registry No. 89790-55-6; Nov. 16, 1984.
CAS Registry No. 89790-53-4; Nov. 16, 1984.
Jacqueline E. Van Muijlwijk-Koezen, et al. (Mar. 1, 2001) J Med Chem 44(5):749-762.
O.H. Chan, et al. (Jul. 1998) "Evaluation of a targeted prodrug strategy to enhance oral absorption of poorly water-soluable compounds." Pharm Research vol. 15(7): 1012-1018.
D. Fleisher, et al. (1996) "Improved oral drug delivery" Advanced Drug Reviews vol. 19: 115-130.
F.D. King (1994) "Bioisosteres, Conformational Restriction, and Pro-Drugs- Case History: An Example of Conformational Restriction Approach." Medicinal Chemistry: Principles and Practice. (Cambridge, RSC, GB) pp. 206-225.
R. Sauer, et al. (e-pub Jan. 22, 2000) "Water-soluble phosphate prodrugs of 1-propargyl-8- styrylxanthine derivatives, A2A-selective adenosine receptor antagonists." J Med Chem vol. 43: 440-448.
Kumar, S., et al., Syntheses and Anthelmintic Activity of Alkyl 5(6)-(Substituted-carbamoyl)- and 5 (6)-(Distributed-carbamoyl) benzimidazole-2-carbamates and Related Compounds, J. Med. Chem., 1984, vol. 27, No. 8, pp. 1083-1089 (CAPLUS Accn. No. 1984:454990).
Varia, S.A. et al., Aug. 1984, "Phenytoin Prodrugs III: Water-Soluble Prodrugs for Oral and/or Parenteral Use", Journal of Pharmaceutical Sciences, 73(8)1068-1073.

* cited by examiner ously used
PRO-DRUGS OF N-THIAZOL-2-YL-BENZAMIDE DERIVATIVES This application claims the benefit of priority under 35 U.S.C. §119(a)-(d) of Danish Application No. PA200500594, filed Apr. 25, 2005, and claims the benefit of priority under 35 U.S.C. §119(e) of U.S. Provisional Application No. 60/675,029, filed Apr. 26, 2005, and of U.S. Provisional Application No. 60/720,963, filed Sep. 26, 2005, and of U.S. Provisional Application No. 60/743,865, filed Mar. 28, 2006, the contents of all of which are hereby incorporated by reference into the subject application.

This application hereby incorporates by reference the Sequence Listing submitted in Computer Readable Form as file 0522-US-NP_Sequence_listing.txt created on Oct. 1, 2009 (811 bytes).

FIELD OF THE INVENTION

The compounds of the present invention are pro-drugs of a class of N-thiazol-2-yl-benzamide derivatives having affinity for the adenosine 2A ($A_{2A}$) receptor. The compounds revert into $A_{2A}$-antagonists, which are useful in the treatment of neurological and psychiatric disorders where an $A_{2A}$-receptor is implicated. Examples of diseases where an $A_{2A}$-receptor is implicated are Parkinson's Disease (PD), Alzheimer's Disease, Huntington's disease (HD), epilepsies, cerebral ischemia, haemorrhagic stroke, neonatal ischemia and hypoxia, subarachnoid haemorrhage, traumatic brain injury, brain damage following cardiac arrest, and for the treatment of depression and psychosis disorders.

BACKGROUND OF THE INVENTION

Adenosine is present in all cells, including neurons and glia, of mammalian organisms where it modulates a variety of important physiological processes. The action of adenosine is mediated by specific receptors, which belong to the family of G protein-coupled receptors. Four adenosine receptors have been cloned and characterized, $A_1$, $A_{2A}$, $A_{2B}$ and $A_3$ (Fredholm B B. et al., *Pharmacol Rev.*, 1994, 46: 143-156). The main intracellular signaling pathways involve the formation of cAMP, with $A_1$ and $A_3$ receptors causing inhibition of adenylate cyclase and $A_{2A}$ and $A_{2B}$ receptors activating it (Olah M., Stiles G L., *Pharmacol. Ther.*, 2000, 85: 55-75).

All of the adenosine receptors have been located in the CNS (Impagnatiello F. et al., *Emerg. Ther. Targets*, 2000, 4: 635-644; Rosin D L. et al., *J. Comp. Neurol.*, 1998, 401: 163-186). The receptor of interest here, $A_{2A}$, is predominantly found in dopamine-rich areas, such as the basal ganglia components; the striatum and the globus pallidus, in various mammals, including humans. The basal ganglia, with the striatum as a central component, are involved in integration of cortical, thalamic and limbic information to produce motor behaviours (for review see Svenningsson P. et al., *Prog. Neurobiol.*, 1999, 59: 355-396).

In the striatum $A_{2A}$ and dopamine $D_2$ receptors are found closely co-localized on the striatopallidal GABAergic neurons, forming the so-called indirect output pathway from the striatum, which is involved in motor inhibition. $A_{2A}$ receptors is believed to contribute to control of motor behaviour by modulating the neurotransmission of GABA, dopamine, acetylcholine and glutamate in various ways. Currently, the interactions between $A_{2A}$ and $D_2$ receptors, and in particular the actions of $A_{2A}$ antagonists, are of great interest in the treatment for Parkinson's disease (PD), which involves a decrease in dopamine levels. The $A_{2A}$ receptors interact tonically and antagonistically with the $D_2$ receptors, causing a decrease in affinity of the $D_2$ receptors for dopamine upon stimulation. Thus, $A_{2A}$ antagonists may be useful as monotherapy for the treatment of Parkinson's disease. Alternatively, $A_{2A}$ antagonists may be capable of enhancing the effect of clinically used dopamine agonists and increase the time-period of dopaminergic drug response. (For details and references therein see e.g.: Richardson P J. et al., *Trends Pharmacol. Sci.*, 1997, 18: 338-344; Svenningsson P. et al., *Prog. Neurobiol.*, 1999, 59: 355-396; Fuxe K. et al., *Parkinson's Dis. Adv.*, 2001, 86: 345-353).

Selective $A_{2A}$ receptor agonists and antagonists have been widely described in pharmacological, behavioural and neuroprotective experiments in rodents and non-human primates (for reviews see: Richardson P J. et al., *Trends Pharmacol. Sci.*, 1997, 18: 338-344; Ribeiro J A. et al., *Prog. Neurobiol.*, 2003, 68: 377-392; Ongini E. et al., *Il Farmaco*, 2001, 56: 87-90; Wardas J., *Polish J. Pharmacology*, 2003, 54: 313-326).

The close interaction of $D_2$ and $A_{2A}$ receptors can be clearly exemplified in models of catalepsy, where $D_2$ receptor antagonists as well as $A_{2A}$ receptor agonists induce catalepsy, which is counteracted by $A_{2A}$ receptor antagonists and $D_2$ receptor agonists, respectively (see Svenningsson P. et al., *Prog. Neurobiol.*, 1999, 59: 355-396 and Refs therein).

Promising anti-parkinsonian effects of $A_{2A}$ receptor antagonists have recently been reported by many investigators. For example, both SCH58261 (2-(2-furanyl)-7-(2-phenylethyl)-7H-pyrazolo[4,3-e][1,2,4]triazolo[1,5-c]pyrimidin-5-amine) and KW-6002 (8-[(1E)-2-(3,4-dimethoxyphenyl)ethenyl]-1,3-diethyl-3,7-dihydro-7-methyl-1H-purine-2,6-dione), enhance contralateral rotations, elicited by a subtreshold dose of levodopa, in unilateral 6-OHDA (6-hydroxydopamine) lesioned mice and rats (See Ongini E. et al., *Drug Dev. Res.*, 2001, 52: 379-386 and references therein). Furthermore, KW-6002 significantly improves motor impairment induced in non-human primates by MPTP, without causing dyskinesias, that is commonly described for long-term treatment with the dopamine agonist L-dopa (Kanda T. et al., *Ann. Neurol.*, 1998, 43: 507-513; Grondin R. et al., Neurology, 1999, 52: 1673-1677; Kanda T. et al., *Exp. Neurol.*, 2000, 162: 321-327).

Thus, $A_{2A}$ receptor antagonists show great potential as future drugs for long-term medication of PD patients, since they seem not only to reverse the motor impairment but also to slow down or stop the progress of the disease by promoting cell survival.

Neuroprotective effects by $A_{2A}$ receptor antagonists have recently been reported in in vivo and in vitro models of different neurodegenerative diseases (for review see: Wardas J., *Pol. J. Pharmacol.*, 2002, 54: 313-26 and Stone T W., *Adv. Exp. Med. Biol.*, 2002, 513: 249-80). $A_{2A}$ antagonists have been shown to be neuroprotective in different PD models like in MPTP (1-methyl-4 phenyl-1,2,3,6-tetrahydropyridine) treated mice and 6-OHDA-lesioned rats. Here, KW-6002 prevented functional loss of dopaminergic nerve terminals in the striatum as well as prevented gliosis normally induced around degenerating neurons (Ikeda K. et al., *J. Neurochem.*, 2002, 80: 262-270; Hirsch E C. et al., *Adv. Neurol.*, 1999, 80: 9-18;

Kanda T. et al., *Ann. Neurology*, 1998, 43 (4): 507-513; Lundblad M. et al., *J. Neurochem.*, 2003, 84(6): 1398-410). Similar results have been obtained in experimental models of Huntington's disease. In rat HD models quinolinic acid or kainate induced lesions were reduced after using adenosine $A_{2A}$ receptor antagonists, with a decrease in striatal cell loss and motor changes (Reggio R. et al., *Brain Res.*, 1999, 831: 315-318; Popoli P. et al., *J. Neurosci.*, 2002, 22: 1967-1975). In addition, $A_{2A}$ receptor antagonists have shown to decrease neuronal cell death after cerebral ischemia in neonatal and adult rats and gerbils (Gao Y., Phillis J W., *Life Sci.*, 1994, 55(3): PL61-5; Monopoli A. et al., *Neuroreport*, 1998, 9(17): 3955-9). $A_{2A}$ knock out animals have been reported to be protected from neonatal hypoxic ischemia and transient focal ischemia (Bona E. et al., *Neuropharnacology*, 1997, 36(9): 1327-1338; Chen J F. et al., *J Neurosci*, 1999, 19(21): 9192-9200) and from 3NP (3-nitropropionic acid) induced, presynaptic, neurotoxic glutamate release (Blum D. et al., *J. Neurosci*, 2003, 23: 5361-5369). The protective effect of $A_{2A}$ antagonists against neurodegeneration by glutamate release has already been shown in a rat model of ischemic damage to the cerebral cortex (Simpson R E., *J Neurochem*, 1992, 58: 1683-1690 and O'Regan M H. et al., Brain Res, 1992, 582: 22-26).

Protection by $A_{2A}$ antagonists has also been reported in primary astrocytes, in a rat model of bFGF induced astrogliosis, an amyloid beta peptide 25-35 induced neurotoxicity in cerebral granule cells (CGCs) and model of QA induced neuronal cell death in rat organotypic slice cultures (Brambilla R. et al., *Glia.*, 2003, 43: 190-194; Dall'Igna O P. et al., *Br. J. Phannacol.*, 2003, 138: 1207-1209; Tebano M T., et al., *Eur. J. Phannacol.*, 2002, 253-257).

Adenosine is involved in modulation of seizures (Dragunow M. et al., *Epilepsia*, 1985, 26: 480-487), and anticonvulsive effects are mainly mediated via $A_1$. $A_{2A}$-antagonist can modulate receptor interaction (O'Kane E M., Stone T W., *Eur. J. Pharm.*, 1998, 362: 17-25) and an $A_{2A}$-antagonist could thereby unmask protective $A_1$ activity in epilepsy (De Sarro G. et al., *Eur. J. Pharmacol.*, 1999, 371(2-3): 137-145; Ongini E. et al., *Ann N Y Acad Sci.*, 1997, 825: 30-48.)

Collectively, $A_{2A}$ receptor antagonists can efficiently protect different neurons from various forms of insult induced neurodegeration (Abbracchio M P., Cattabeni F., *Ann N Y Acad Sci.*, 1999, 890: 79-92; Ongini E. et al., *Ann N Y Acad Sci.*, 1997, 825: 30-48).

Adenosine and its analogues induce "depressant-like" effects in animal models of psychiatric disorders (Minor T R. et al., *Behav Neurosci.*, 1994, 108: 265-276; Woodson J C. et al., *Behav Neurosci.*, 1998, 112: 399-409). Moreover, these behavioural deficits were found to be reversed by adenosine $A_{2A}$ receptor antagonists (Minor T R. et al., *Behav. Brain Res.*, 2001, 120: 203-212). Further studies have shown that treatment with adenosine or 2-chloroadenosine increased immobility time in the mouse forced swimming test, another animal model of depression generally considered reliable (Porsolt R D. et al., *Arch Int Pharmacodyn Ther.*, 1977, 229: 327-336).

Several compounds with dual affinity for $A_{2A}$ and $A_1$ receptor subtypes, known as the 4-amino[1,2,3]triazolo[4,3-a]quinoxalines, has been shown to be active in the rat forced swimming test (Sarges R. et al., *J Med Chem*, 1990, 33: 2240-2254) indicating antidepressant activity of the substances. Most recently, $A_{2A}$ receptor knockout mice were found to be less sensitive to "depressant" challenges than their wildtype littermates (El Yacoubi M. et al., *Br J Pharmacol.*, 2001, 134: 68-77). Consistent with this data, the $A_{2A}$ receptor antagonists SCH58261 and KW6002 reduced the total immobility time in the mouse tail suspension test (El Yacoubi M. et al., *Br J Pharmacol.*, 2001, 134: 68-77). The antagonists SCH58261 and ZM241385 4-(2-[7-amino-2-(2-furyl)[1,2,4]triazolo[2,3-a][1,3,5]triazin-5-ylamino]-ethyl) phenol were also found to reduce immobility when administered to mice previously screened for having high immobility time, while SCH58261 reduced immobility of mice that were selectively bred for their "helplessness" in this model (El Yacoubi M. et al., *Br. J. Pharmacol.*, 2001, 134: 68-77).

Studies using $A_{2A}$ knock-out mice suggest that these animals show a blunted response to psycho-stimulants such as amphetamine and cocaine, despite the fact that their expression and binding affinities of D1 and D2 receptors are unaffected (Chen J F. et al., *Neurosci.*, 2000, 97: 195-204). Moreover, inactivation of $A_{2A}$ receptors has been shown to selectively attenuate amphetamine-induced behavioural sensitisation (Chen J F. et al., *Neuropsychopharmacol.*, 2003, 28: 1086-1095). In addition, $A_{2A}$ knockout mice show reduced startle and PPI of the acoustic startle (Wang J H. et al., *Behav. Brain Res.*, 2003, 143: 201-207), measures often used to detect antipsychotic activity. Further support is found in studies where pharmacological blockade of $A_{2A}$ receptors with a selective antagonist completely abolished pre-pulse inhibition (PPI) (Nagel J. et al., *Synapse*, 2003, 49: 279-286). Psychostimulants, such as MK-801 and amphetamine failed to disrupt startle and PPI in $A_{2A}$ KO mice (Wang J H. et al., *Behav. Brain Res.*, 2003, 143: 201-207).

Thus, the available evidence suggests that adenosine $A_{2A}$ receptor antagonists, by specifically modulating mesostriatal or mesocorticolimbic dopaminergic pathways, may possess antidepressant and/or antipsychotic properties.

Bastia et al. describes in Neurosci Lett. Aug. 16, 2002;328 (3):241-4 a study of the effects of A(1) and A(2A) adenosine receptor ligands in a mouse models of pain. Several publications concern the relating between the A2A receptor and sleep, e.g. Gallopin T. et al., 2005, Neuroscience 134, 1377-1390 and Huang Z. L. et al. 2005, Nat. Neurosci 8, 858-859, and Methippara M. M. et al., 2005, Am. J Physiol Regul. Integr. Comp. Physiol 289, R1715-R1723.

In the following, examples of publications concerning different uses of $A_{2A}$ receptor antagonists are given. US 20040138235 suggests use of $A_{2A}$ receptor antagonists for treatment of restless leg syndrome (RLS). WO 02/055083 suggest use of $A_{2A}$ receptor antagonist for Attention Deficit Hyperactivity Disorder (ADHD). Benefits of Adenosine $A_{2A}$ receptor antagonists for cognition is suggested in: Prediger R. D. S. et al., Behavioral Pharmacology 2005, Vol 16, No 4, 209-218 and Prediger R. D. S. et al. Behavioral Brain Research 2005, 159, 197-205. A review by Jacobson K. A. and Gao Z. *Nature Reviews, Drug Discovery*, 2006, Vol. 5, 247-264 relates to adenosine receptors as therapeutic targets, and suggests among other the use of $A_{2A}$ receptor antagonist for migraine, alcohol abuse and RLS.

SUMMARY OF THE INVENTION

The objective of the present invention is to provide prodrugs with improved aqueous solubility of compounds, which are antagonists at the $A_{2A}$ receptor.

Accordingly, the present invention relates to a compound with formula I

A-B-Z     I wherein Z is a group with formula II

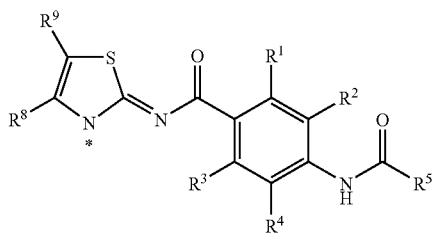

or Z is a group with formula IIa

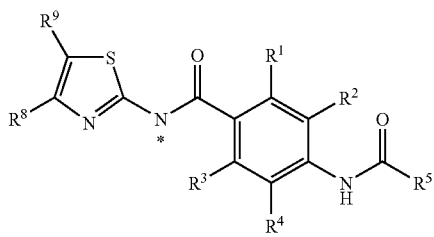

wherein $R^1$-$R^4$ are independently selected from hydrogen, halogen, $C_{1-6}$-alkyl and $C_{1-6}$-alkoxy;

$R^5$ is selected from the group consisting of $C_{1-8}$-alkyl, $C_{3-8}$-cycloalkyl-$C_{1-6}$-alkyl, $C_{3-8}$-cycloalkyl and $C_{1-6}$-alkyl-phenyl;

$R^8$ and $R^9$ are independently selected from the group consisting of hydrogen, halogen and $C_{1-6}$-alkyl;

* indicates the atom attached to B;

A is a solvating group;

B is a linking moiety or a bond;

or pharmaceutically acceptable addition salts thereof.

The invention in further aspects relates to a compounds with formula I as defined above, which compound revert under physiological conditions into a compound with general formula V,

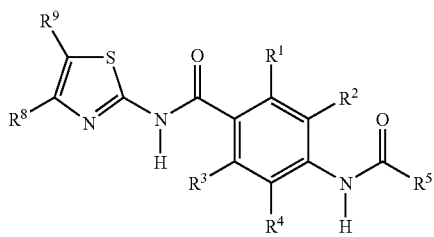

wherein $R^1$-$R^5$ and $R^8$-$R^9$ have the same meaning as defined herein for Compound I.

In a third aspect the present invention relates to the use of a compound with formula I as defined above, for the manufacture of a medicament for the treatment of a disease where an $A_{2A}$-receptor is implicated.

In a fourth the present invention relates to a pharmaceutical composition comprising a compound with formula I as defined above.

In a further aspect the present invention relates to a method of treating a disease where an $A_{2A}$-receptor is implicated, comprising administration of a therapeutically acceptable amount of a compound with formula I, as defined above.

DETAILED DESCRIPTION OF THE INVENTION

WO 2005/039572 describes N-thiazol-2-yl-benzamide derivatives having affinity for the adenosine 2A ($A_{2A}$) receptor. The inventors have now found that some N-thiazol-2-yl-benzamide derivatives having high affinity for the $A_{2A}$ receptor as $A_{2A}$ antagonists, are characterized by low aqueous solubility and that these compounds can be prepared as bio-reversible pro-drugs with significantly improved aqueous solubility.

Limited aqueous solubility of potential drug candidates may severely hamper their development into medicaments. For example, preclinical toxicology and safety studies of a drug candidate requires dose escalation to obtain high exposure levels, and therefore, these studies may by hampered by a low solubility of the drug candidate.

Derivatisation of a drug as a bio-reversible pro-drug is a means of overcoming various barriers for a drug to reach its site of action (for a general reference, see: *Design of Pro-drugs*, ed. H. Bundgaard, Elsevier, Amsterdam, 1985; also see Ettmayer P. et al., *J. Med. Chem.*, 2004, 47: 2393-2404). Derivatisation of an insoluble drug as a water soluble, bio-reversible pro-drug is an example of this concept (Fleisher D. et al., *Advanced Drug Delivery Reviews*, 1996, 19: 115-130). Some drugs or drug candidates have been derivatised as esters of amino acids or phosphoric acid, either via a linker (e.g. Varia S. A. and Stella V. J. *J. Pharm. Sci.* 1984, 73:8, 1080-87) or by direct attachment to the drug or drug candidate (see e.g. Chan H. O. et al. *Pharmaceutical Research* 1998, 15:7, 1012-18) to improve their solubility and bioavailability. Likewise, glucose conjugates have been shown to have increased absorption characteristics (Mizuma T. et al *Biochemical Pharmacology* 1992, 43:9, 2037-39. Also, an $A_{2A}$ antagonist has previously been derivatised as a prodrug (Sauer R. et al *J. Med. Chem* 2000, 43, 440-48).

Accordingly, the present invention relates to compounds with formula I as defined above.

In particular embodiments, the invention relates to compounds with formula I as defined herein, wherein $R^1$ is hydrogen or a $C_{1-6}$-alkoxy, e.g. methoxy. The invention also relates to compounds with formula I as defined herein, wherein $R^2$ is selected from the group consisting of hydrogen, halogen, e.g. fluoro, chloro or bromo, $C_{1-6}$-alkyl, e.g. $C_{1-3}$-alkyl e.g. methyl, and $C_{1-6}$-alkoxy, e.g. methoxy. The invention also relates to compounds with formula I as defined herein, wherein $R^3$ is hydrogen. The invention further relates to compounds with formula I as defined herein, wherein $R^4$ is hydrogen or halogen, e.g. fluoro or chloro.

In another particular embodiment, the present invention relates to compounds with formula I as defined herein, wherein $R^1$-$R^4$ are independently selected from hydrogen, halogen, e.g. fluoro, chloro or bromo, $C_{1-6}$-alkyl, e.g. $C_{1-3}$-alkyl, e.g. methyl, and $C_{1-6}$-alkoxy, e.g. methoxy.

In further embodiments, $R^1$ and $R^3$ are independently selected from the group consisting of hydrogen and $C_{1-6}$-alkoxy, e.g. $C_{1-3}$-alkoxy, e.g. methoxy. One embodiment of the invention relates to compounds of formula I as defined herein wherein both $R^1$ and $R^3$ are hydrogen. In further embodiments, one or both of $R^1$ and $R^3$ is a $C_{1-6}$-alkoxy, e.g. $C_{1-3}$-alkoxy, e.g. methoxy, while both $R^2$ and $R^4$ are hydrogen.

The invention also relates to compounds of the invention, characterised in that $R^2$ and $R^4$ are independently selected from the group consisting of hydrogen, halogen, e.g. chloro or fluoro, and $C_{1-6}$-alkyl, e.g. $C_{1-3}$-alkyl, e.g. methyl. In further embodiments, $R^2$ and $R^4$ are independently selected from halogen, e.g. fluoro or chloro, and $C_{1-6}$-alkyl, e.g. $C_{1-3}$-alkyl, e.g. methyl, and $R^1$ and $R^3$ are hydrogen. In further embodiments, both $R^2$ and $R^4$ are hydrogen.

In another particular embodiment the present invention relates to compounds with formula I as defined herein, wherein $R^1$ is $C_{1-6}$ alkoxy, e.g. $C_{1-3}$ alkoxy, e.g. methoxy, and $R^4$ is selected from the group consisting of halogen, e.g. fluoro or chloro, and $C_{1-6}$-alkyl, e.g. $C_{1-3}$-alkyl, e.g. methyl. The invention also relates to compounds of formula I as defined herein, wherein $R^1$ is a $C_{1-6}$-alkoxy, e.g. $C_{1-3}$-alkoxy, e.g. methoxy, and $R^4$ is a halogen, e.g. fluoro or chloro, or a $C_{1-6}$-alkyl, e.g. a $C_{1-3}$-alkyl, e.g. methyl, and $R^2$ and $R^3$ are hydrogen.

In another particular embodiment the present invention relates to compounds with formula I as defined herein, wherein $R^1$ is $C_{1-6}$-alkoxy, e.g. $C_{1-3}$-alkoxy, e.g. methoxy and $R^2$ is selected from the group consisting of halogen, e.g. fluoro or chloro, and $C_{1-6}$-alkyl, e.g. $C_{1-3}$-alkyl, e.g. methyl.

In another particular embodiment the present invention relates to compounds with formula I as defined herein, wherein $R^1$ is $C_{1-6}$-alkoxy, e.g. $C_{1-3}$-alkoxy, e.g. methoxy and $R^2$ and $R^4$ are independently selected from the group consisting of halogen, e.g. fluoro or chloro, and $C_{1-6}$-alkyl, e.g. $C_{1-3}$-alkyl, e.g. methyl.

In a more particular embodiment the present invention relates to compounds with formula I as defined herein, wherein $R^5$ is selected from the group consisting of $C_{1-8}$-alkyl, preferably $C_{3-8}$-alkyl and even more preferred $C_{4-8}$-alkyl which, preferably, is branched at the β-position, $C_{3-8}$-cycloalkyl-$C_{1-6}$-alkyl, preferably $C_{3-8}$-cycloalkyl-methyl, $C_{3-8}$-cycloalkyl and $C_{1-6}$-alkyl-phenyl, preferably methylphenyl. In further embodiments of the invention, $R^5$ is a $C_{4-8}$-alkyl branched at the β-position, e.g. neopentyl or isobutyl.

In a particular embodiment the present invention relates to compounds with formula I as defined herein, wherein $R^8$-$R^9$ are independently selected from the group consisting of hydrogen, halogen, preferably fluoro or chloro, and $C_{1-6}$-alkyl, e.g. $C_{1-3}$-alkyl, preferably methyl.

In another particular embodiment the present invention relates to compounds with formula I as defined herein, wherein both $R^8$ and $R^9$ are hydrogen.

Within the invention is also a compound of formula I, wherein said compound is selected from the group of compounds I with Z having formula II, wherein:
  $R^1=R^2=R^3=R^4=R^8=R^9=H$ and $R^4=$neopentyl;
  $R^1=R^3=R^4=R^8=R^9=H$, $R^2=Cl$ and $R^5=$cyclopentylmethyl;
  $R^1=R^3=R^4=R^8=R^9=H$, $R^2=Br$ and $R^5=$neopentyl;
  $R^1=R^3=R^8=R^9=H$, $R^2=R^4=F$ and $R^5=$neopentyl;
  $R^1=R^3=R^4=R^8=R^9=H$, $R^2=F$ and $R^5=$neopentyl;
  $R^1=R^3=R^4=R^8=R^9=H$, $R^2=$methyl and $R^5=$neopentyl;
  $R^1=R^3=R^4=R^8=R^9=H$, $R^2=$methoxy and $R^5=$neopentyl;
  $R^2=R^3=R^4=R^8=R^9=H$, $R^1=$methoxy and $R^5=$isopropyl;
  $R^2=R^3=R^8=R^9=H$, $R^1=$methoxy, $R^4=Cl$ and $R^5=$phenylmethyl;
  $R^2=R^3=R^8=R^9=H$, $R^1=$methoxy, $R^4=Cl$ and $R^5=$cyclopentyl;
  $R^1=R^3=R^4=R^8=R^9=H$, $R^2=F$ and $R^5=$isobutyl; and
  $R^1=R^3=R^8=R^9=H$, $R^2=R^4=Cl$ and $R^5=$neopentyl.

In preferred embodiments, the invention relates to compounds of formula I with Z having formula II, wherein $R^1=R^2=R^3=R^4=R^8=R^9=H$ and $R^5=$neopentyl. In further embodiments, the invention relates to compounds of formula I with Z having formula II, wherein $R^1=R^3=R^8=R^9=H$, $R^2=R^4=F$ and $R^5=$neopentyl.

In further embodiments, the invention relates to compounds of formula I with Z having formula II, wherein $R^1=R^3=R^8=R^9=H$, $R^2=R^4=F$ and $R^5=$neopentyl. The invention also relates to compounds of formula I with Z having formula II, wherein $R^1=R^3=R^4=R^8=R^9=H$, $R^2=F$ and $R^5=$neopentyl.

As indicated herein the solvating group A is a group capable of supplying improved aqueous solubility of said compound I compared to the corresponding compound with formula V as defined herein. As described herein B of Compound I is a linking moiety or a bond.

The invention also relates to compounds of the invention, wherein the construct A-B- of said prodrug of formula I is capable of providing improved aqueous solubility of said compound I, compared to the corresponding compound with formula V as defined herein, and in which construct A-B- in the context of Compound I, one or more bonds will be cleaved under physiological conditions, to release said compound with formula V.

In further embodiments of the invention, A-B- of formula I is a phosphoric acid mono methylenyl ester [i.e. a mono methylenyl ester of phosphoric acid, e.g. as A-B- in the following compound of formula I: "Phosphoric acid mono-{2-[(E/Z)-4-(3,3-dimethyl-butyrylamino)-benzoylimino]-thiazol-3-ylmethyl}ester"] and Z of formula I is, e.g., a group with formula II as defined herein.

In another particular embodiment the present invention relates to compounds with formula I as defined herein, wherein A is a solvating group selected from compounds containing at least two functionalities, wherein one of said functionalities is a ionisable functionality, and another of said functionalities is a functionality which can form a bond to B; or A is selected from compounds containing a suitable number of hydroxy functionalities, and a functionality which can form a bond to B.

The invention also relates to compounds with formula I as defined herein, wherein A is a solvating group selected from the group consisting of: N-unsubstituted or N-mono-, N-di-, or N-tri-substituted amino acids, di-amines, mono-, di- or tri-phosphates or esters thereof and/or salts thereof, sulfonic acids or salts thereof, di-carboxylic acids or salts thereof, O- or N-glycosides, polyalcohols including alditols and ketols; or combinations thereof, such as glycosylated amino acids or glycosylated phosphates.

In another particular embodiment, the present invention relates to compounds with formula I as defined herein, wherein A is a solvating group selected from N-unsubstituted, N-mono- or N-di-substituted amino acids (e.g. selected from the group consisting of the 20 naturally occurring biogenic amino acids or N-mono- or dialkylated analogues hereof, 4-carboxy-piperidine, or α-methyl valine), mono-phosphate mono esters, or salts thereof, or A is a polyalcohol (e.g. glycerol) or a carbohydrate (e.g. glucose).

In further embodiments the present invention relates to compounds with formula I as defined herein, wherein B is a linking moiety with formula III, IV or IVa

III

-continued

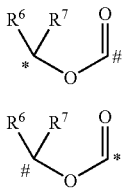

wherein $R^{6-7}$ are independently selected from hydrogen and $C_{1-6}$-alkyl, and * indicates the atom attached to Z, and # indicates the atom attached to A.

In a particular embodiment, the present invention relates to compounds with formula I as defined herein, wherein B is a linking moiety with formula III or IV.

Further embodiments of the present invention relates to compounds with formula I as defined herein, wherein Z is a group with formula II

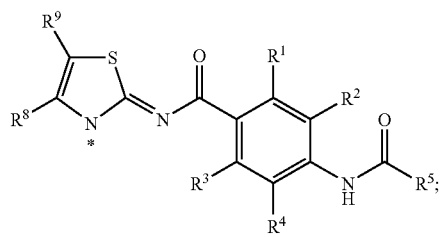

* indicating the atom attached to B, wherein $R^1$-$R^5$ and $R^8$-$R^9$ are as defined herein.

In a further embodiment, the present invention relates to compounds with formula I as defined herein, where B is a linking moiety with formula III or IV

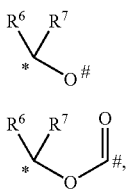

* indicating the atom attached to Z, and # indicating the atom attached to A, preferably Z being a group with formula II.

In particular embodiments, the present invention relates to compounds with formula I as defined herein, wherein Z is a group with formula II and B is a linking moiety with formula III or IV, provided that when B is a linking moiety with formula III, A is attached via a carbonyl or a hetero carbonyl group, or as an acetal or ketal; and provided that when B is a linking moiety with formula IV, A is attached via a nitrogen or an oxygen atom; wherein $R^{6-7}$ are independently selected from hydrogen and $C_{1-6}$-alkyl, preferably methyl; and * indicates the atom attached to Z, and # indicates the atom attached to A.

In yet another particular embodiment the present invention relates to compounds with formula I as defined herein, wherein B is a linking moiety with formula III or IV and both $R^6$ and $R^7$ are hydrogen or $R^6$ is hydrogen and $R^7$ is methyl.

In yet another particular embodiment the present invention relates to compounds with formula I as defined herein, wherein B is a linking moiety with formula III or IV and $R^{6-7}$ are hydrogen.

In a further embodiment, the present invention relates to compounds with formula I as defined herein where B is a linking moiety with formula IVa

provided that A is attached via a nitrogen or an oxygen atom; wherein $R^{6-7}$ are independently selected from hydrogen and $C_{1-6}$-alkyl, e.g. $C_{1-3}$-alkyl, preferably methyl, provided that $R^6$ and $R^7$ are not both hydrogen;

and * indicates the atom attached to Z, and # indicates the atom attached to A.

In yet another particular embodiment the present invention relates to compounds with formula I as defined herein, wherein B is a linking moiety with formula IVa and $R^6$ is hydrogen and $R^7$ is methyl.

In yet another particular embodiment the present invention relates to compounds with formula I as defined herein, wherein B is a bond, provided that A is a carbohydrate attached via the anomeric carbon atom.

In a more particular embodiment the present invention relates to compounds with formula I as defined herein, wherein Z is a group with formula II and B is a bond, provided that A is a carbohydrate attached via the anomeric carbon atom.

In particular, the present invention relates to a compound with formula I as defined above, wherein one or more bonds of said compound are degraded, e.g. enzymatically or chemically, under physiological conditions, and that upon said degradation a compound with formula V,

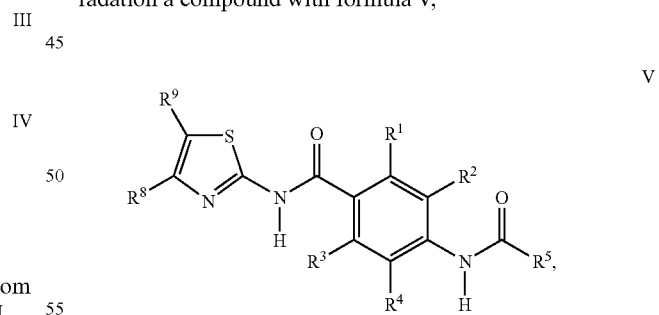

wherein $R^1$-$R^5$ and $R^8$-$R^9$ have the same meaning as defined herein for compound I, will be released.

In preferred embodiments, the compound of the invention with formula I as defined herein, revert under physiological conditions into a $A_{2A}$ receptor antagonist with the general formula V, preferably having a human $A_{2A}$ binding affinity ($K_i$) of 200 nM or less, more preferred of 50 nM or less, and most preferred of 10 nM or less.

In a broad aspect, the invention relates to compounds with formula I as defined herein, which revert under physiological conditions into $A_{2A}$ receptor ligands with the general formula V, preferably having a human $A_{2A}$ binding affinity ($K_i$) of 200 nM or less, more preferred of 50 nM or less, and most preferred of 10 nM or less.

In specific embodiments, the compound I with formula I as defined herein has an aqueous solubility which is at least 2 or at least 5 or at least 10 or at least 20 times higher than compared to the corresponding compound V.

AS indicated above it is understood that the various embodiments of compound I described herein with respect to $R^1$-$R^5$ and $R^8$-$R^9$ also applies to compound V. In specific embodiments of Compound I, V is selected from the group consisting of:

4-(3,3-Dimethyl-butyrylamino)-N-thiazol-2-yl-benzamide;
3-Chloro-4-(2-cyclopentyl-acetylamino)-N-thiazol-2-yl-benzamide;
3-Bromo-4-(3,3-dimethyl-butyrylamino)-N-thiazol-2-yl-benzamide;
4-(3,3-Dimethyl-butyrylamino)-3,5-difluoro-N-thiazol-2-yl-benzamide;
4-(3,3-Dimethyl-butyrylamino)-3-fluoro-N-thiazol-2-yl-benzamide;
4-(3,3-Dimethyl-butyrylamino)-3-methyl-N-thiazol-2-yl-benzamide;
5-Chloro-2-methoxy-4-(2-methyl-benzoylamino)-N-thiazol-2-yl-benzamide;
5-Chloro-4-(cyclopentanecarbonyl-amino)-2-methoxy-N-thiazol-2-yl-benzamide;
3-Fluoro-4-(3-methyl-butyrylamino)-N-thiazol-2-yl-benzamide;
4-(3,3-Dimethyl-butyrylamino)-3-methoxy-N-thiazol-2-yl-benzamide;
4-Isobutyrylamino-2-methoxy-N-thiazol-2-yl-benzamide; and
4-(3,3-Dimethyl-butyrylamino)-3,5-dichloro-N-thiazol-2-yl-benzamide, or a salt thereof.

Particular compounds of the invention are a compound of formula I or a salt thereof selected from the group consisting of:

Amino-acetic acid 2-[(E/Z)-4-(3,3-dimethyl-butyrylamino)-benzoylimino]-thiazol-3-ylmethyl ester,
2-Amino-3-methyl-butyric acid 2-[(E/Z)-3-chloro-4-(2-cyclopentyl-acetylamino)-benzoylimino]-thiazol-3-ylmethyl ester, e.g. (S)-2-Amino-3-methyl-butyric acid 2-[(E/Z)-3-chloro-4-(2-cyclopentyl-acetylamino)-benzoylimino]-thiazol-3-ylmethyl ester;
2-Amino-3-methyl-butyric acid 2-[(E/Z)-3-bromo-4-(3,3-dimethyl-butyrylamino)-benzoylimino]-thiazol-3-ylmethyl ester, e.g. (S)-2-Amino-3-methyl-butyric acid 2-[(E/Z)-3-bromo-4-(3,3-dimethyl-butyrylamino)-benzoylimino]-thiazol-3-ylmethyl ester;
2-Amino-3-methyl-butyric acid 2-[(E/Z)-4-(3,3-dimethyl-butyrylamino)-3,5-difluoro-benzoylimino]-thiazol-3-ylmethyl ester, e.g. (S)-2-Amino-3-methyl-butyric acid 2-[(E/Z)-4-(3,3-dimethyl-butyrylamino)-3,5-difluoro-benzoylimino]-thiazol-3-ylmethyl ester;
2-Amino-3-methyl-butyric acid 2-[(E/Z)-4-(3,3-dimethyl-butyrylamino)-3-fluoro-benzoylimino]-thiazol-3-ylmethyl ester, e.g. (S)-2-Amino-3-methyl-butyric acid 2-[(E/Z)-4-(3,3-dimethyl-butyrylamino)-3-fluoro-benzoylimino]-thiazol-3-ylmethyl ester;
2-Amino-3-methyl-butyric acid 2-[(E/Z)-4-(3,3-dimethyl-butyrylamino)-3-methyl-benzoylimino]-thiazol-3-ylmethyl ester, e.g. (S)-2-Amino-3-methyl-butyric acid 2-[(E/Z)-4-(3,3-dimethyl-butyrylamino)-3-methyl-benzoylimino]-thiazol-3-ylmethyl ester;
2-Amino-3-methyl-butyric acid 2-[(E/Z)-4-(3,3-dimethyl-butyrylamino)-benzoylimino]-thiazol-3-ylmethyl ester, e.g. (S)-2-Amino-3-methyl-butyric acid 2-[(E/Z)-4-(3,3-dimethyl-butyrylamino)-benzoylimino]-thiazol-3-ylmethyl ester;
2-Amino-3-methyl-butyric acid 2-[(E/Z)-5-chloro-2-methoxy-4-(2-methyl-benzoylamino)-benzoylimino]-thiazol-3-ylmethyl ester, e.g. (S)-2-Amino-3-methyl-butyric acid 2-[(E/Z)-5-chloro-2-methoxy-4-(2-methyl-benzoylamino)-benzoylimino]-thiazol-3-ylmethyl ester;
2-Amino-3-methyl-butyric acid 2-[(E/Z)-5-chloro-4-(cyclopentanecarbonyl-amino)-2-methoxy-benzoylimino]-thiazol-3-ylmethyl ester, e.g. (S)-2-Amino-3-methyl-butyric acid 2-[(E/Z)-5-chloro-4-(cyclopentanecarbonyl-amino)-2-methoxy-benzoylimino]-thiazol-3-ylmethyl ester;
2-Amino-3-methyl-pentanoic acid 2-[(E/Z)-3-chloro-4-(2-cyclopentyl-acetylamino)-benzoylimino]-thiazol-3-ylmethyl ester, e.g. (2S,3S)-2-Amino-3-methyl-pentanoic acid 2-[(E/Z)-3-chloro-4-(2-cyclopentyl-acetylamino)-benzoylimino]-thiazol-3-ylmethyl ester;
2-Amino-3-methyl-pentanoic acid 2-[(E/Z)-3-bromo-4-(3,3-dimethyl-butyrylamino)-benzoylimino]-thiazol-3-ylmethyl ester, e.g. (2S,3S)-2-Amino-3-methyl-pentanoic acid 2-[(E/Z)-3-bromo-4-(3,3-dimethyl-butyrylamino)-benzoylimino]-thiazol-3-ylmethyl ester;
2-Amino-3-methyl-pentanoic acid 2-[(E/Z)-3-fluoro-4-(3-methyl-butyrylamino)-benzoylimino]-thiazol-3-ylmethyl ester, e.g. (2S,3S)-2-Amino-3-methyl-pentanoic acid 2-[(E/Z)-3-fluoro-4-(3-methyl-butyrylamino)-benzoylimino]-thiazol-3-ylmethyl ester;
2-Amino-3-methyl-pentanoic acid 2-[(E/Z)-4-(3,3-dimethyl-butyrylamino)-3,5-difluoro-benzoylimino]-thiazol-3-ylmethyl ester, e.g. (2S,3S)-2-Amino-3-methyl-pentanoic acid 2-[(E/Z)-4-(3,3-dimethyl-butyrylamino)-3,5-difluoro-benzoylimino]-thiazol-3-ylmethyl ester;
2-Amino-3-methyl-pentanoic acid 2-[(E/Z)-4-(3,3-dimethyl-butyrylamino)-3-fluoro-benzoylimino]-thiazol-3-ylmethyl ester, e.g. (2S,3S)-2-Amino-3-methyl-pentanoic acid 2-[(E/Z)-4-(3,3-dimethyl-butyrylamino)-3-fluoro-benzoylimino]-thiazol-3-ylmethyl ester;
2-Amino-)-3-methyl-pentanoic acid 2-[(E/Z)-4-(3,3-dimethyl-butyrylamino)-benzoylimino]-thiazol-3-ylmethyl ester, e.g. (2S,3S)-2-Amino-)-3-methyl-pentanoic acid 2-[(E/Z)-4-(3,3-dimethyl-butyrylamino)-benzoylimino]-thiazol-3-ylmethyl ester;
2-Amino-3-methyl-pentanoic acid 2-[(E/Z)-4-(3,3-dimethyl-butyrylamino)-3-methoxy-benzoylimino]-thiazol-3-ylmethyl ester, e.g. (2S,3S)-2-Amino-3-methyl-pentanoic acid 2-[(E/Z)-4-(3,3-dimethyl-butyrylamino)-3-methoxy-benzoylimino]-thiazol-3-ylmethyl ester;
Pyrrolidine-2-carboxylic acid 2-[(E/Z)-3-bromo-4-(3,3-dimethyl-butyrylamino)-benzoylimino]-thiazol-3-ylmethyl ester, e.g. (S)-Pyrrolidine-2-carboxylic acid 2-[(E/Z)-3-bromo-4-(3,3-dimethyl-butyrylamino)-benzoylimino]-thiazol-3-ylmethyl ester;
Pyrrolidine-2-carboxylic acid 2-[(E/Z)-3-chloro-4-(2-cyclopentyl-acetylamino)-benzoylimino]-thiazol-3-ylmethyl ester, e.g. (S)-Pyrrolidine-2-carboxylic acid 2-[(E/Z)-3-chloro-4-(2-cyclopentyl-acetylamino)-benzoylimino]-thiazol-3-ylmethyl ester;
Pyrrolidine-2-carboxylic acid 2-[(E/Z)-3-fluoro-4-(3-methyl-butyrylamino)benzoylimino]-thiazol-3-ylmethyl ester, e.g. (S)-Pyrrolidine-2-carboxylic acid 2-[(E/Z)-3-fluoro-4-(3-methyl-butyrylamino)benzoylimino]-thiazol-3-ylmethyl ester;
Pyrrolidine-2-carboxylic acid 2-[(E/Z)-4-(3,3-dimethyl-butyrylamino)-3-fluoro-benzoylimino]-thiazol-3-ylmethyl ester, e.g. (S)-Pyrrolidine-2-carboxylic acid 2-[(E/Z)-4-(3,3-dimethyl-butyrylamino)-3-fluoro-benzoylimino]-thiazol-3-ylmethyl ester;

Pyrrolidine-2-carboxylic acid 2-[(E/Z)-4-(3,3-dimethyl-butyrylamino)-3-methoxy-benzoylimino]-thiazol-3-ylmethyl ester, e.g. (S)-Pyrrolidine-2-carboxylic acid 2-[(E/Z)-4-(3,3-dimethyl-butyrylamino)-3-methoxy-benzoylimino]-thiazol-3-ylmethyl ester;

Pyrrolidine-2-carboxylic acid 2-[(E/Z)-4-(3,3-dimethyl-butyrylamino)-3-methyl-benzoylimino]-thiazol-3-ylmethyl ester, e.g. (S)-Pyrrolidine-2-carboxylic acid 2-[(E/Z)-4-(3,3-dimethyl-butyrylamino)-3-methyl-benzoylimino]-thiazol-3-ylmethyl ester;

Amino-2-methyl-propionic acid 2-[(E/Z)-4-(3,3-dimethyl-butyrylamino)-3-methoxy-benzoylimino]-thiazol-3-ylmethyl ester, e.g. 2-Amino-2-methyl-propionic acid 2-[(E/Z)-4-(3,3-dimethyl-butyrylamino)-3-methoxy-benzoylimino]-thiazol-3-ylmethyl ester;

2-Amino-2-methyl-propionic acid 2-[(E/Z)-3-fluoro-4-(3-methyl-butyrylamino)-benzoylimino]-thiazol-3-ylmethyl ester;

2-Amino-2-methyl-propionic acid 2-[(E/Z)-4-(3,3-dimethyl-butyrylamino)-3-fluoro-benzoylimino]-thiazol-3-ylmethyl ester;

Piperidine-4-carboxylic acid 2-[(E/Z)-4-isobutyrylamino-2-methoxy-benzoylimino]-thiazol-3-ylmethyl ester;

Piperidine-4-carboxylic acid 2-[(E/Z)-3-bromo-4-(3, 3-dimethyl-butyrylamino)-benzoylimino]-thiazol-3-ylmethyl ester;

Piperidine-4-carboxylic acid 2-[(E/Z)-3-chloro-4-(3-ethyl-hexanoylamino-benzoylimino]-thiazol-3-ylmethyl ester;

Piperidine-4-carboxylic acid 2-[(E/Z)-3-fluoro-4-(3-methyl-butyrylamino)-benzoylimino]-thiazol-3-ylmethyl ester;

Piperidine-4-carboxylic acid 2-[(E/Z)-4-(3,3-dimethyl-butyrylamino)-3-methyl-benzoylimino]-thiazol-3-ylmethyl ester;

Piperidine-4-carboxylic acid 2-[(E/Z)-5-chloro-2-methoxy-4-(2-methyl-benzoylamino)-benzoylimino]-thiazol-3-ylmethyl ester, Piperidine-4-carboxylic acid 2-[(E/Z)-5-chloro-4-(cyclopentanecarbonyl-amino)-2-methoxy-benzoylimino]-thiazol-3-ylmethyl ester;

3-Amino-propionic acid 2-[(E/Z)-4-(3,3-dimethyl-butyrylamino)-3,5-difluoro-benzoylimino]-thiazol-3-ylmethyl ester;

2-Methylamino-propionic acid 2-[(E/Z)-4-(3,3-dimethyl-butyrylamino)-3,5-difluoro-enzoylimino]-thiazol-3-ylmethyl ester, e.g. (S)-2-Methylamino-propionic acid 2-[(E/Z)-4-(3,3-dimethyl-butyrylamino)-3,5-difluoro-enzoylimino]-thiazol-3-ylmethyl ester;

2-Amino-2,3-dimethyl-butyric acid 2-[(E/Z)-4-(3,3-dimethyl-butyrylamino)-3,5-difluoro-benzoylimino]-thiazol-3-ylmethyl ester, e.g. (R,S)-2-Amino-2,3-dimethyl-butyric acid 2-[(E/Z)-4-(3,3-dimethyl-butyrylamino)-3,5-difluoro-benzoylimino]-thiazol-3-ylmethyl ester;

2-Dimethylamino-3-methyl-pentanoic acid 2-[(E/Z)-4-(3,3-dimethyl-butyrylamino)-3,5-difluoro-benzoylimino]-thiazol-3-ylmethyl ester, e.g. (2S,3S)-2-Dimethylamino-3-methyl-pentanoic acid 2-[(E/Z)-4-(3,3-dimethyl-butyrylamino)-3,5-difluoro-benzoylimino]-thiazol-3-ylmethyl ester;

Phosphoric acid mono-{2-[(E/Z)-4-(3,3-dimethyl-butyrylamino)-benzoylimino]-thiazol-3-ylmethyl}ester;

Phosphoric acid mono-{2-[(E/Z)-4-(3,3-dimethyl-butyrylamino)-3-fluoro-benzoylimino]-thiazol-3-ylmethyl}ester;

Phosphoric acid mono-{2-[(E/Z)-3,5-dichloro-4-(3,3-dimethyl-butyrylamino)-benzoylimino]-thiazol-3-ylmethyl}ester;

Phosphoric acid mono-{2-[(E/Z)-4-(3,3-dimethyl-butyrylamino)-3,5-difluoro-benzoylimino]-thiazol-3-ylmethyl}ester;

Carbonic acid 2,3-dihydroxy-propyl ester 2-[(E/Z)-4-(3,3-dimethyl-butyrylamino)-3,5-difluoro-benzoylimino]-thiazol-3-ylmethyl ester, e.g. (R,S)-Carbonic acid 2,3-dihydroxy-propyl ester 2-[(E/Z)-4-(3,3-dimethyl-butyrylamino)-3,5-difluoro-benzoylimino]-thiazol-3-ylmethyl ester;

4-(3,3-Dimethyl-butyrylamino)-3,5-difluoro-N-{3-[3,4,5-trihydroxy-6-((R)-hydroxymethyl)-tetrahydro-pyran-2-yloxymethyl]-3H-thiazol-2-ylidene}-benzamide, e.g. 4-(3,3-Dimethyl-butyrylamino)-3,5-difluoro-N-{3-[(1S,3S,4S,5R)-3,4,5-trihydroxy-6-((R)-hydroxymethyl)-tetrahydro-pyran-2-yloxymethyl]-3H-thiazol-2-ylidene}-benzamide; and 4-(3,3-Dimethyl-butyrylamino)-3,5-difluoro-N-[3-(3,4,5-trihydroxy-6-hydroxymethyl-tetrahydro-pyran-2-yl)-3H-thiazol-2-ylidene]-benzamide, e.g. 4-(3,3-Dimethyl-butyrylamino)-3,5-difluoro-N-[3-((2R,3R,4S,5S,6R)-3,4,5-trihydroxy-6-hydroxymethyl-tetrahydro-pyran-2-yl)-3H-thiazol-2-ylidene]-benzamide.

One embodiment of the invention relates to the use of a compound according to the present invention for the manufacture of a medicament for the treatment of a disease where an $A_{2A}$-receptor is implicated, e.g. a disease described herein.

Further embodiments relates to the use of a compound according to the present invention for the manufacture of a medicament for the treatment of a disease or disorder selected from the group consisting of Parkinson's Disease, Alzheimer's Disease, Huntington's disease, epilepsies, cerebral ischemia, haemorrhagic stroke, neonatal ischemia and hypoxia, subarachnoid haemorrhage, traumatic brain injury, brain damage following cardiac arrest, depression, Restless Leg Syndrome (RLS), abuse, e.g. alcohol abuse, migraine, somnolence, narcolepsy, pain, Attention Deficit Hyperactivity Disorder (ADHD), neurodegenerative diseases, cognitive deficits, memory problems and psychosis disorders, e.g. schizophrenia or for enhancement of cognition or as a neuroprotective.

The invention also relates to the use of a compound of the invention for the manufacture of a medicament for the treatment in a patient with Parkinson's disease of a condition selected from the group consisting of RLS, depression, cognitive deficits and memory problems.

The invention further relates to a method of treating or preventing a disease or disorder where an $A_{2A}$-receptor is implicated, comprising administration of a therapeutically acceptable amount of a compound of the invention.

In particular, the invention relates to a method of treating a disease or a disorder selected from the group consisting of Parkinson's Disease, Alzheimer's Disease, Huntington's disease, epilepsies, cerebral ischemia, haemorrhagic stroke, neonatal ischemia and hypoxia, subarachnoid haemorrhage, traumatic brain injury, brain damage following cardiac arrest, depression, somnolence, narcolepsy, pain, Attention Deficit Hyperactivity Disorder (ADHD), and psychosis disorders, e.g. schizophrenia, comprising administration of a therapeutically acceptable amount of a compound of the invention.

In particular, the invention relates to a method of treating or preventing Parkinson's Disease comprising administration of a therapeutically acceptable amount of a compound of the invention.

Further embodiment of the invention relates to the use of a compound of the invention for symptomatic treatment of early Parkinson's disease as monotherapy. The invention further relates to the use of a Compound of the invention as adjunct to another medicament for Parkinson disease, e.g. levodopa, in advanced Parkinson's disease, thereby, e.g., increasing the time-period of dopaminergic drug response.

A further aspect of the invention relates to the use of a compound V, wherein V, i.e. including $R^1$-$R^5$ and $R^8$-$R^9$, is as defined herein for compound I,

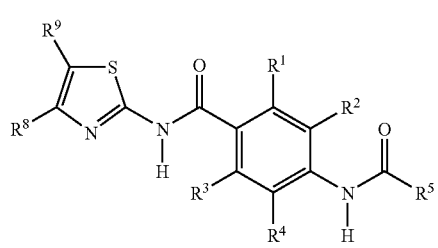

for the manufacture of a medicament for the treatment of a disease selected from the group consisting of RLS, schizophrenia, abuse, e.g. alcohol abuse, migraine, pain, somnolence, narcolepsy, ADHD, neurodegenerative diseases, and cognitive deficits, memory problems or for enhancement of cognition or as a neuroprotective.

The invention also relates to the use of compound V as defined above for the manufacture of a medicament for the treatment in a patient with Parkinson's disease of a condition selected from the group consisting of RLS, depression, cognitive deficits and memory problems.

Further embodiment of the invention relates to the use of a use of a compound V as defined herein for symptomatic treatment of early Parkinson's disease as monotherapy. The invention further relates to the use of a Compound of the invention as adjunct to another medicament for Parkinson disease, e.g. levodopa (L-dopa), at advanced Parkinson's disease, thereby, e.g., increasing the time-period of dopaminergic drug response.

In specific embodiments of the invention described herein for the medical use of compound V, the compound V is selected from the group consisting of
4-(3,3-Dimethyl-butyrylamino)-N-thiazol-2-yl-benzamide;
3-Chloro-4-(2-cyclopentyl-acetylamino)-N-thiazol-2-yl-benzamide;
3-Bromo-4-(3,3-dimethyl-butyrylamino)-N-thiazol-2-yl-benzamide;
4-(3,3-Dimethyl-butyrylamino)-3,5-difluoro-N-thiazol-2-yl-benzamide;
4-(3,3-Dimethyl-butyrylamino)-3-fluoro-N-thiazol-2-yl-benzamide;
4-(3,3-Dimethyl-butyrylamino)-3-methyl-N-thiazol-2-yl-benzamide;
5-Chloro-2-methoxy-4-(2-methyl-benzoylamino)-N-thiazol-2-yl-benzamide;
5-Chloro-4-(cyclopentanecarbonyl-amino)-2-methoxy-N-thiazol-2-yl-benzamide;
3-Fluoro-4-(3-methyl-butyrylamino)-N-thiazol-2-yl-benzamide;
4-(3,3-Dimethyl-butyrylamino)-3-methoxy-N-thiazol-2-yl-benzamide;
4-Isobutyrylamino-2-methoxy-N-thiazol-2-yl-benzamide; and
4-(3,3-Dimethyl-butyrylamino)-3,5-dichloro-N-thiazol-2-yl-benzamide; or a salt thereof.

As used herein the term treatment include prevention or treatment or relief as the case may be. Also the term disease may mean a disorder or disease as the case may be.

When referring to the uses of the compound of the invention it is understood that the Compound may, e.g., be in the form of a salt.

The compounds of the general formula I and V may exist as enantiomers thereof and such enantiomers are also embraced by the invention. Throughout the specification and claims, reference to specific compounds with formula V refers to the racemates unless otherwise indicated.

The term $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl, and 2-methyl-1-propyl. The term $C_{1-8}$-alkyl refers similarly to branched or unbranched alkyl group having from one to eight carbon atoms inclusive.

The term $C_{3-8}$-cycloalkyl designates a monocyclic or bicyclic carbocycle having three to eight C-atoms, such as cyclopropyl, cyclopentyl, cyclohexyl, etc.

Halogen means fluoro, chloro, bromo or iodo.

The terms $C_{1-6}$-alkoxy, $C_{3-8}$-cycloalkyl-$C_{1-6}$-alkyl, designate such groups in which the $C_{1-6}$-alkyl and the $C_{3-8}$-cycloalkyl group are as defined above.

The acid addition salts of the compounds of the invention are pharmaceutically acceptable salts formed with non-toxic acids. Exemplary of such organic salts are those with maleic, fumaric, benzoic, ascorbic, succinic, oxalic, bis-methylene-salicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The base addition salts of the compounds of the invention are pharmaceutically acceptable salts formed with non-toxic bases. Exemplary of such base addition salts include salts with alkali metals (e.g. sodium, potassium); salts with alkaline earth metals (e.g. calcium, magnesium); ammonium salts; salts with organic amines and the like.

The term solvating group means any group, which can supply improved aqueous solubility to a compound with formula V, upon conjugation to a compound with formula V as described above.

The term linking moiety means any construct, which can serve to connect A and Z as defined above, characterized in that upon conversion of a pro-drug with formula I under physiological conditions, a compound with formula V will be released.

The term physiological conditions means any set of chemical or enzymatic conditions, which can be encountered in a living mammalian organism. Exemplary of such chemical or enzymatic conditions are the chemical and enzymatic conditions of the gastro-intestinal tract, i.e. the stomach, intestinal lumen and at the gut wall; in blood; or various tissues or organs such as the liver.

The term amino acid means any chemical compound, which contains a carboxylic acid functionality and an amino functionality, such as an a-cyclic or cyclic alkyl-amine, or an aromatic ring containing a nitrogen atom.

The term di-amine means any compound, which contains an amino functionality, which can form a bond to B, and an ionisable amino functionality.

The term hetero carbonyl means any equivalent of the carbonyl group; such as a carbon atom connected to a heteroatom other than oxygen via a double bond; or a heteroatom, such as phosphorous or sulphur, connected to an oxygen atom via a double bond.

The term (E/Z), wherein E and Z have the standard meanings "entgegen" and "zusammen", means a pure double bond stereo isomer of unknown geometry, or a mixture of stereoisomers in any ratio.

The pharmaceutical compositions of this invention, may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg. The total daily dose is usually in the range of about 0.05-500 mg, and most preferably about 0.1 to 50 mg of the active compound of the invention.

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Typical examples of recipes for the formulation of the invention are as follows:

| 1) Tablets containing 0.5 mg of a compound of the invention calculated as free base or free acid: | |
|---|---|
| Compound I | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |
| 2) Tablets containing 0.5 mg of a compound of the invention calculated as free base or free acid: | |
| Compound I | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |
| 3) Syrup containing per milliliter: | |
| Compound I | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |
| 4) Solution for injection containing per milliliter: | |
| Compound I | 0.5 mg |
| Sorbitol | 5.1 mg |
| Acetic Acid | 0.05 mg |
| Saccharin sodium | 0.5 mg |
| Water | ad 1 mL |

The compounds of the invention may be prepared by the following general methods:

a) Deprotection of a compound with formula VIII

A'-B-Z,   VIII wherein Z and B have the same meaning as described above, A' is a suitably protected form of A, and A is as described above, to release a compound with formula I as described above.

Deprotection of compounds with formula VIII may be performed by standard procedures known to chemists skilled in the art. This includes deprotection of compounds with formula VIII, in which said suitable protecting group(s) are acid labile, by treatment with a suitable acid in a suitable solvent at a suitable temperature, such as i.e. HCl in diethyl ether at 20-40° C., or trifluoroacetic acid in dichloromethane at 20-40° C., followed by evaporation of solvent and excess acid. Alternatively, deprotection of compounds with formula VIII, in which said suitable protecting group(s) are base labile, includes treatment with a suitable base such as sodium methoxide in methanol at 20-40° C., followed by neutralization with a suitable acid, such as acidic ion exchange resins.

b) Reaction of a compound with formula I

A-B-Z   I wherein Z and B are as described above, and A is an N-unsubstituted or N-mono-substituted amino acid, with an alkylating agent such as an aldehyde in the presence of a reducing agent such as sodium cyanoborohydride (NaCNBH$_4$), in a suitable solvent such as methanol (MeOH), at a suitable temperature such as room temperature.

Compounds with formula VIII may be prepared by the following general methods:

a) Reaction of a compound with formula V

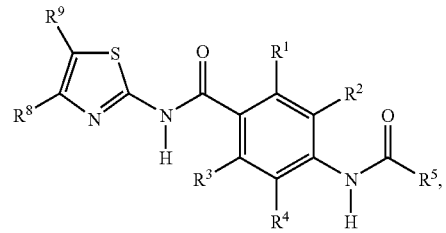

V wherein $R^1$-$R^5$ and $R^8$-$R^9$ are as described above, with a compound A'-B-E under basic conditions, wherein A' is a suitably protected from of A, and A and B are as defined above, and where E is attached to the atom in B with label *, and E is a leaving group such as e.g. chloride.

The reaction of compounds with formula V with a compound A'-B-E may be performed by standard procedures known to chemists skilled in the art. This includes deprotonation of compounds with formula V by reaction with a suitable base such as sodium hydride (NaH) in a suitable solvent such as dimethyl formamide (DMF) at a suitable temperature such as 20-60° C., or 1,8-diazabicyclo[5.4.0]undec-7-ene (DBU) in tetrahydrofurane (THF) at 60° C., followed by addition of A'-B-E.

b) Reaction of a compound with formula VII

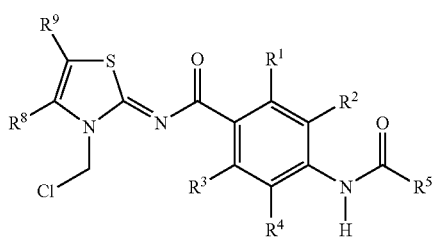

wherein $R^1$-$R^5$ and $R^8$-$R^9$ are as described above, with a compound A'-H, wherein A' is a suitably protected form of A, and A is as defined above and H is a proton.

The reaction of compounds with formula VII with a compound A'-H may be performed by standard procedures known to chemists skilled in the art. This includes deprotonation of compounds A'-H by reaction with a suitable base such as diisopropylethylamine, in a suitable solvent such as THF, followed by addition of a compound with formula VII, at a suitable temperature such as 20-50° C., or by reaction of compounds A'-H with a compound with formula VII in the presence of a suitable catalyst such as silver trifluorosulphonate (AgOTf), in a suitable solvent such as dichloromethane, at a suitable temperature, such as −78° C.-20° C.

c) Reaction of a compound with formula V

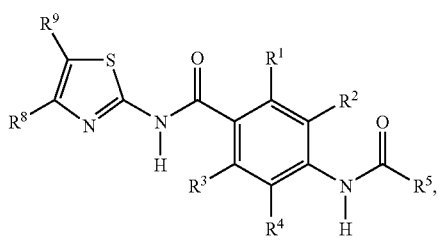

wherein $R^1$-$R^5$ and $R^8$-$R^9$ are as described above, with a compound A'-E wherein A' is a suitably protected form of A, and A is as defined above, and E is a leaving group such as e.g. chloride.

The reaction of compounds with formula V with a compound A'-E may be performed by standard procedures known to chemists skilled in the art. This includes reaction of compounds A'-E with a compound with formula V in the presence of a suitable catalyst such as AgOTf, in a suitable solvent such as dichloromethane, at a suitable temperature, such as −78° C.-20° C.

Compounds with formula V were prepared according to the following general procedure as outlined below.

Coupling of a compound with formula VI

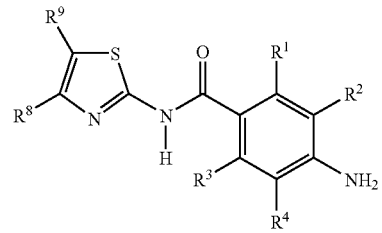

wherein $R^1$-$R^4$ and $R^8$-$R^9$ are as described above, with a carboxylic acid $R^5$—COOH or carboxylic acid chloride $R^5$—COCl, wherein $R^5$ is as defined above.

The coupling of compounds with formula VI with carboxylic acids $R^5$—COOH may be performed by standard procedures known to chemists skilled in the art. This includes coupling in the presence of a uronium salt coupling reagent and diisopropyethylamine (DIPEA), at temperatures between 20-80° C., in a suitable polar or apolar solvent such as N-methyl pyrrolidinone (NMP) or 1,2-dichloroethane. The coupling of compounds with formula VI with carboxylic acid chlorides $R^5$—COCl may be performed by standard procedures known to chemists skilled in the art. This includes coupling of starting materials with formula VI with carboxylic acid chlorides $R^5$—COCl in the presence of a suitable base such as pyridine at temperatures between 20-60° C. in a suitable solvent such as 1,2-dichloroethane.

Compounds with formula VI were prepared according to standard procedures known to chemists skilled in the art as outlined below. Suitably substituted 4-nitro benzoic acid chlorides were either commercially available or prepared by chlorination of the corresponding carboxylic acids with oxalyl chloride or sulfonyl chloride, and were coupled with suitably substituted 2-aminothiazoles in a suitable solvent such as 1,2-dichloroethane in the presence of a suitable base such as pyridine, at a suitable temperature between 20-60° C. The products were then reduced to the corresponding anilines by procedures known to chemists skilled in the art, such as catalytic hydrogenation using hydrogen and a suitable catalyst such as 10% Pd/C in a suitable solvent such as ethanol. Alternatively, suitably substituted 4-amino benzoic acids were coupled with suitably substituted 2-aminothiazoles in the presence of a carbodiimide coupling reagent such as 1-(3-dimethylaminopropyl)-3-ethyl-carbodiimide hydrochloride in the presence of a suitable additive such as 1-hydroxybenzotriazole in a suitable solvent such as 1,2-dichloroethane in the presence of a suitable base such as DIPEA, at a suitable temperature between 20-60° C.

Compounds A'-B-E in which A' is a suitably protected amino acid, E is chlorine, and B is a structure with formula III, wherein E is attached to the atom with label *, and $R^{6-7}$ is hydrogen, were prepared according to standard procedures known to chemists skilled in the art as outlined below. Suitably N- and side chain protected amino acids were saponified using a suitable base such as cesium carbonate in a suitable solvent such as mixed water and ethanol, or tetrabutyl ammonium hydrogen sulphate in a suitable solvent mixture such as a mixture of water and dichloromethane. The amino acid salt thus formed is next reacted with a suitable reagent such as bromochloromethane or chloromethylene chlorosulfonic acid in a suitable solvent such as dimethoxyethane at a suitable temperature such as room temperature, or under phase transfer conditions in a suitable solvent mixture such as a mixture of water and dichloromethane, at a suitable temperature such as room temperature.

Compounds A'-B-E in which A' is a suitably protected poly-alcohol, E is chlorine, and B is a structure with formula IV, wherein E is attached to the atom with label *, and $R^{6-7}$ is hydrogen, were prepared according to standard procedures known to chemists skilled in the art as outlined below. Suitably protected poly-alcohols were reacted with a suitably substituted chloroalkyl chloroformate in a suitable solvent such as chloroform in the presence of a suitable base such as pyridine, at a suitable temperature between 20-60° C.

Compounds of formula VII, wherein $R^1$-$R^4$ and $R^8$-$R^9$ are as described above, were prepared according to standard procedures known to chemists skilled in the art. This includes reaction of a compound with formula V, wherein $R^1$-$R^5$ and $R^8$-$R^9$ are as described above, with chloromethylchloroformate in the presence of a suitable base such as NaH in a suitable solvent such as DMF at a suitable temperature such as 20-60° C.

Alternatively, the compounds of formula VII, wherein $R^1$-$R^4$ and $R^8$-$R^9$ are as described above, can be prepared by reaction of a compound with formula V, wherein $R^1$-$R^5$ and $R^8$—$R^9$ are as described above, with a substance $ClCH_2$-E, wherein E is a suitable leaving group, for example bromine or chlorosulfonate, in the presence of a suitable base such as NaH in a suitable solvent such as DMF at a suitable temperature such as 20-60° C.

EXAMPLES

Analytical Methods

Analytical LC-MS data were obtained by either of two methods: (method A): on a PE Sciex API 150EX instrument equipped with an IonSpray source and a Shimadzu LC-8A/SLC-10A LC system. Column: 30×4.6 mm Waters Symmetry C18 column with 3.5 µm particle size; solventsystem: A=water/trifluoroacetic acid (100:0.05) and B=water/acetonitrile/trifluoroacetic acid (5:95:0.03); method: Linear gradient elution with 90% A to 100% B in 4 min and with a flow rate of 2 ml/min. or (method B): on a Micromass LCT instrument equipped with a 4-way MUX ElectroSpray source, a Micromass Waters MUX-2488 UV-detector, a Sedex 754 4-channels LT-ELS-detector, a CTC Analytics HTS-PAL autosampler equipped with 4 injection valves, and 4 Waters 1525 Binary HPLC pumps. Column: 30×4.6 mm Waters Symmetry C18 column with 3.5 µm particle size; solventsystem: A=water/trifluoroacetic acid (100:0.05) and B=water/acetonitrile/trifluoroacetic acid (5:95:0.03); method: Linear gradient elution with 90% A to 100% B in 4 min and with a flow rate of 2 ml/min. Purity was determined by integration of the UV (254 nm) and ELSD traces. The retention times (RT) are expressed in minutes.

$^1$H NMR spectra were recorded at 500.13 MHz on a Bruker Avance DRX500 instrument or at 250.13 MHz on a Bruker AC 250 instrument. Deuterated dimethyl sulfoxide (99.8% D) was used as solvent unless otherwise specified. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, br s=broad singlet and br=broad signal.

For column chromatography silica gel of the type Kieselgel 60, 40-60 mesh ASTM was used.

Example 1

Preparation of Intermediates

Chloromethylen chlorosulphonic acid was prepared as described in Binderup, E. and Hansen, E. T. *Synthetic Communications* 1984, 14, 857-64.

Preparation of Compounds with Formula A'-B-E

A compound A'-B-E in which A is a suitably protected mono phosphate, E is chlorine and B is a structure with formula III, wherein E is attached to the atom with label *, and $R^{6-7}$ is hydrogen, was prepared as described by J. P. Krise et al. *J. Med. Chem.* 1999, 42, pp. 3094-3100. (Di-tert-butyl chloromethyl phosphate).

Compounds A'-B-E in which A' is an N-blocked, and optionally side chain protected amino acid, E is chlorine and B is a structure with formula III, wherein E is attached to the atom with label *, and $R^{6-7}$ is hydrogen, were prepared as described by P. Gomes et al. *Synthetic Communications*, 2003, 33, (10), pp. 1683-1693, or alternatively as described by Harada, N. et al. in *Synthetic Communications*, 1994, 24, 767-772. (N-blocked amino acid chloro methylene esters)

The following were prepared analogously:

3-tert-Butoxycarbonylamino-propionic acid chloromethyl ester:

1H NMR ($D_6$-DMSO): 1.37 (s, 9H); 2.54 (t, 2H); 3.18 (dt, 2H); 5.83 (s, 2H); 6.88 (br t, 1H).

(S)-2-tert-Butoxycarbonyl-methyl-amino-propionic acid chloromethyl ester:

1H NMR ($D_6$-DMSO): 1.35 (s, 9H); 1.40 (s, 3H); 2.74-2.82 (3H); 4.35-4.66 (1H); 5.84-5.94 (2H).

(R,S)-2-tert-Butoxycarbonylamino-2,3-dimethyl-butyric acid chloromethyl ester:

1H NMR ($D_6$-DMSO): 0.82 (d, 3H); 0.89 (d, 3H); 1.29 (s, 3H); 1.36 (s, 9H); 1.99 (m, 1H); 5.85 (br s, 2H); 7.19 (br, 1H).

(R,S)-Carbonic acid chloromethyl ester 2,2-dimethyl-[1,3]dioxolan-4-ylmethyl ester:

(R,S)-(2,2-Dimethyl-[1,3]dioxolan-4-yl)-methanol (8 mmol) was dissolved in chloroform (100 mL) and pyridine (8 mmol) was added. Chloromethyl chloroformate (15 mmol) was added dropwise, and the reaction mixture was stirred at ambient temperature for 4 h. The reaction mixture was washed with water, the organic phase was dried over $MgSO_4$ and evaporated. The crude product was purified by flash chromatography on silica using 10% ethylacetate in heptane as eluent.

Yield: 30%

1H NMR ($D_6$-DMSO): 1.28 (s, 3H); 1.34 (s, 3H); 3.72 (dd, 1H); 4.05 (dd, 1H); 4.18 (m, 1H); 4.30-4.35 (m, 2H); 5.93 (s, 2H).

Preparation of the Intermediates with Structure VII

1i  N-(3-Chloromethyl-3H-thiazol-2-ylidene)-4-(3,3-dimethyl-butyrylamino)-3,5-difluoro-benzamide NaH (20 mmol) was suspended in DMF (100 mL) and 4-(3,3-dimethyl-butyrylamino)-3,5-difluoro-N-thiazol-2-yl-benzamide (17 mmol) was added and stirred at ambient temperature for 1.5 h, then chloromethylene chloroformate (51 mmol) was added and the reaction mixture was stirred overnight at room temperature. The solvent was removed by evaporation and the crude reaction product was partitioned between ethyl acetate and water. The organic phase was washed with NH$_4$Cl (aq., sat.) ×2 and water ×1, dried over MgSO$_4$, filtered and evaporated. The crude product was purified by flash chromatography on silica using a gradient from 10% to 20% ethyl acetate in heptane as eluent.

Yield: 86%

1H NMR (D$_6$-DMSO): 1.05 (s, 9H); 2.26 (s, 2H); 6.30 (s, 2H); 7.18 (d, 1H); 7.75 (d, 1H); 7.92 (d, 2H); 9.75 (s, 1H).

LC/MS (m/z) 402 (MH+).

Preparation of the Intermediates with Structure VI

1a: 4-Amino-N-thiazol-2-yl-benzamide

2-Aminothiazole (100 mmol) was suspended in 1,2-dichloroethane (200 mL) and pyridine (100 mmol) was added. The mixture was added portionwise to a suspension of 4-nitro benzoic acid chloride (150 mmol) in 1,2-dichloroethane (500 mL) and stirred at 60° C. over night. The reaction mixture was cooled and filtered. The filtrate was washed with 1,2-dichloroethane and dried in vacuo to give 4-nitro-N-thiazol-2-yl-benzamide.

Yield: 96%

1H NMR (D$_6$-DMSO): 7.33 (d, 1H); 7.60 (d, 1H); 8.26-8.41 (4H); 12.96 (br s, 1H).

4-Nitro-N-thiazol-2-yl-benzamide (28 mmol) was suspended in abs. EtOH (400 mL) and ethyl acetate (200 mL) and glacial acetic acid (50 mL) was added followed by 10% Pd/C (0.5 g). The mixture was hydrogenated for 72 h at 3 bar H$_2$. The hydrogenation mixture was filtered, and the solvent was removed under reduced pressure. The crude product was added NaHCO$_3$ (sat.) and ethyl acetate, the remaining solid fraction was removed by filtration and dried in vacuo. The liquid phases were separated, the organics were washed with brine, dried over MgSO$_4$, filtered and evaporated to yield a solid. The solid fractions were combined.

Yield: 83% (80% overall).

1H NMR (D$_6$-DMSO): 5.93 (s, 2H); 6.50 (d, 2H); 7.18 (d, 1H); 7.49 (d, 1H); 7.84 (d, 2H); 12.05 (br s, 1H).

1b: 4-Amino-3-methyl-N-thiazol-2-yl-benzamide:

4-Nitro-3-methyl-benzoic acid (83 mmol) was suspended in 1,2-dichloroethane (500 mL) and dimethylformamide (DMF) (5 mL) under an argon atmosphere. Oxalylchloride (2M in dichloromethane, 62.3 mL) was added slowly to the stirred suspension. After stirring at room temperature for 1 h, the solvent was removed by evaporation under reduced pressure, and the reaction mixture was re-dissolved in 1,2-dichloroethane (400 mL). A suspension of 2-aminothiazole (83 mmol) and pyridine (83 mmol) in 1,2-dichloroethane (100 mL) was added portionwise. The reaction mixture was stirred at 50° C. over night. The solvent was removed under reduced pressure and the solids were re-suspended in ethyl acetate (500 mL) and NaHCO$_3$ (sat.) (500 mL). The solids were removed by filtration and the liquid phases were separated. The organic phase was washed with NaHCO$_3$ (sat.), dried over MgSO$_4$, filtered and evaporated. The crude product was re-crystallized from ethyl acetate and the product fractions were combined to give 4-nitro-3-methyl-N-thiazol-2-yl-benzamide.

Yield: 76%.

1H NMR (D$_6$-DMSO): 2.58 (s, 3H); 7.33 (d, 1H); 7.60 (d, 1H); 8.10 (d, 2H); 8.20 (d, 2H); 12.92 (br s, 1H).

4-Nitro-3-methyl-N-thiazol-2-yl-benzamide (63 mmol) was suspended in abs. EtOH (200 mL) and ethyl acetate (100 mL) and glacial acetic acid (10 mL) was added followed by 10% Pd/C (1 g). The mixture was hydrogenated over night at 3 bar H$_2$. The hydrogenation mixture was filtered and the solvent was removed under reduced pressure. The crude product was added NaHCO$_3$ (sat.) and ethyl acetate, the remaining solid fraction was removed by filtration and dried in vacuo. The liquid phases were separated, the organics were washed with brine, dried over MgSO$_4$, filtered and evaporated to yield the product as a solid.

Yield: 95% (72% overall)

1H NMR (D$_6$-DMSO): 2.09 (s, 3H); 5.71 (s, 2H); 6.63 (d, 1H); 7.17 (d, 1H); 7.39 (d, 1H); 7.69-7.81 (m,2H); 11.96(brs, 1H).

The following compounds were prepared analogously:

1c: 4-Amino-3-methoxy-N-thiazol-2-yl-benzamide:

Yield: 17%

1H NMR (D$_6$-DMSO): 3.85 (s, 3H); 5.59 (s, 2H); 6.67 (d, 1H); 7.19 (d, 1H); 7.48-7.65 (3H); 12.17 (br s, 1H).

1d: 4-Amino-3-fluoro-N-thiazol-2-yl-benzamide:

4-Nitro-3-fluoro benzoic acid (535 mmol) was dissolved in toluene (500 mL) and tetrahydrofuran (THF) (75 mL). SOCl$_2$ (930 mmol) was added and the mixture was heated at 65° C. for 5 h. The reaction mixture was cooled and the solvent removed by evaporation. The residue was re-dissolved in 1,2-dichloroethane. This solution was added dropwise to a suspension of 2-aminothiazole (480 mmol) and DIPEA (370 mmol) in 1,2-dichloroethane (1 L) with mechanical stirring, while the temperature was kept at 45° C. Upon complete addition the reaction mixture was heated at 60° C. for 1.5 h, then allowed to cool to room temperature and stirred over night. The reaction mixture was filtered, the solids were washed with 1,2-dichloroethane and dried in vacuo to give 4-nitro-3-fluoro-N-thiazol-2-yl-benzamide.

Yield: 35%

1H NMR (D$_6$-DMSO): 7.34 (d, 1H); 7.61 (d, 1H); 8.10 (m, 1H); 8.23 (m, 1H); 8.31 (m, 1H); 13.00 (br, 1H).

4-Nitro-3-fluoro-N-thiazol-2-yl-benzamide (7.5 mmol) was suspended in EtOH (abs., 60 mL) and ethyl acetate (30 mL), glacial acetic acid (5 mL) and 10% Pd/C (300 mg) was added, and the mixture was hydrogenated for 12 days under 3 bar H$_2$. The reaction mixture was filtered and evaporated, and re-dissolved in ethyl acetate (100 mL) and NaHCO$_3$ (sat., 60 mL). The aqueous phase was adjusted to basic pH with NaOH (1M) and the phases were separated. The organic phase was washed with brine, dried over MgSO$_4$, filtered and evaporated.

Yield: 85% (30% overall) 1H NMR (D$_6$-DMSO): 6.00 (s, 2H); 6.80 (t, 1H); 7.21 (d, 1H); 7.51 (d, 1H); 7.74 (m, 1H); 7.81 (m, 1H); 12.19 (s, 1H).

1e: 4-Amino-3-chloro-N-thiazol-2-yl-benzamide:

4-Amino-3-chloro-benzoic acid methyl ester (21.6 mmol) was saponified in EtOH (25 ml) and NaOH (1M, 25 ml) at reflux for 2 h. The organic solvent was evaporated and pH adjusted to 4. The product was removed by filtration, washed with water and dried in vacuo to give 4-amino-3-chloro-benzoic acid.

Yield: 92%

1H NMR (D$_6$-DMSO): 6.15 (s, 2H); 6.79 (d, 1H); 7.59 (dd, 1H); 7.71 (d, 1H); 12.37 (br s, 1H).

4-Amino-3-chloro-benzoic acid (19.8 mmol) was dissolved in DMF (10 mL) and 1,2-dichloroethane (80 mL). DIPEA (19.8 mmol), 1-(3-dimethylaminopropyl)-3-ethyl-carbodiimide hydrochloride (19.8 mmol), 1-hydroxybenzotriazole (19.8 mmol) and 2-aminothiazole (19.8 mmol) was added, and the reaction mixture was stirred at 60° C. over night. The volume was reduced in vacuo, and water (60 mL) was added. The mixture was extracted with ethyl acetate, the organic phase was washed with $NH_4Cl$ (aq., sat.), dried over $MgSO_4$, filtered and evaporated. The crude product was purified by flash chromatography on silica using gradient elution (heptane/ethyl acetate).

Yield: 42% (39% overall)

1H NMR ($D_6$-DMSO): 6.19 (s, 2H); 6.83 (d, 1H); 7.21 (d, 1H); 7.52 (d, 1H); 7.83 (dd, 1H); 8.07 (d, 1H); 12.24 (br s, 1H).

1f: 4-Amino-3-bromo-N-thiazol-2-yl-benzamide:

4-Amino-benzoic acid (100 mmol) was dissolved in DMF (50 mL) and N-bromosuccinimide (100 mmol) was added. Stirred at ambient temperature for 18 h, the reaction mixture was then poured into water (100 mL). The product was removed by filtration, washed with water and dried in vacuo to give 4-amino-3-bromo-benzoic acid.

Yield: 70%

1H NMR ($D_6$-DMSO): 6.10 (s, 2H); 6.78 (d, 1H); 7.63 (dd, 1H); 7.89 (d, 1H); 12.39 (br s, 1H).

4-Amino-3-bromo-benzoic acid (18.5 mmol) was dissolved in DMF (10 mL) and 1,2-dichloroethane (80 mL). DIPEA (18.5 mmol), 1-(3-dimethylaminopropyl)-3-ethyl-carbodiimide hydrochloride (18.5 mmol), 1-hydroxybenzotriazole (18.5 mmol) and 2-aminothiazole (18.5 mmol) was added and the reaction mixture was stirred at 60° C. over night. The volume was reduced in vacuo, and water (60 mL) was added. The mixture was extracted with ethyl acetate, the organic phase was washed with $NH_4Cl$ (aq., sat.), dried over $MgSO_4$, filtered and evaporated. The crude product was purified by flash chromatography on silica using gradient elution (heptane/ethyl acetate).

Yield: 33% (23% overall)

1H NMR ($D_6$-DMSO): 6.14 (s, 2H); 6.82 (d, 1H); 7.21 (d, 1H); 7.51 (d, 1H); 7.86 (dd, 1H); 8.22 (d, 1H); 12.24 (br s, 1H).

1g: 4-Amino-S-chloro-2-methoxy-N-thiazol-2-yl-benzamide:

4-Amino-5-chloro-2-methoxy-benzoic acid (19.8 mmol) ) was dissolved in DMF (10 mL) and 1,2-dichloroethane (80 mL). DIPEA (19.8 mmol), 1-(3-dimethylaminopropyl)-3-ethyl-carbodiimide hydrochloride (19.8 mmol), 1-hydroxy-benzotriazole (19.8 mmol) and 2-aminothiazole (19.8 mmol) was added and the reaction mixture was stirred at 60° C. over night. The volume was reduced in vacuo, and water (60 mL) was added. The mixture was extracted with ethyl acetate, the organic phase was washed with $NH_4Cl$ (aq., sat.), dried over $MgSO_4$, filtered and evaporated. The crude product was re-crystallized from ethyl acetate.

Yield: 32%

1H NMR ($D_6$-DMSO): 3.94 (s, 3H); 6.30 (s, 2H); 6.56 (s, 1H); 7.23 (d, 1H); 7.49 (d, 1H); 7.76 (s, 1H); 11.05 (br s, 1H).

The following compound was prepared analogously:

1h: 4-Amino-3,5-difluoro-N-thiazol-2-yl-benzamide:

Yield: 27%

LC/MS (m/z) 256 (MH+); RT=1.9 (method A).

Example 2

Preparation of the $A_{2A}$ Ligands with Formula V

Examples

2a: 4-(3,3-Dimethyl-butyrylamino)-3-methoxy-N-thiazol-2-yl-benzamide

To 200 μL of a 0.2 M stock solution of 4-amino-3-methoxy-N-thiazol-2-yl-benzamide in 1,2-dichloroethane/DMF, containing 1.2 mmol pyridine per mmol 4-amino-3-methoxy-N-thiazol-2-yl-benzamide, was added 0.05 mmol of 3,3-dimethyl-butyric acid chloride. The reaction mixture was incubated at ambient temperature for 2 h. Purification was performed by preparative HPLC-MS.

1H NMR ($D_6$-DMSO): 1.03 (s, 9H); 2.35 (s, 2H); 3.95 (s, 3H); 7.26 (d, 1H); 7.56 (d, 1H); 7.71 (dd, 1H); 7.79 (d, 1H); 8.19 (d, 1H); 9.14 (s, 1H); 12.55 (br s, 1H).

LC/MS (m/z) 348 (MH+); RT=2.68 (method A).

The following compounds were prepared analogously:

2b: 4-(3,3-Dimethyl-butyrylamino)-N-thiazol-2-yl-benzamide:

LC/MS (m/z) 318 (MH+); RT=2.54 (method A).

2c: 4-(3,3-Dimethyl-butyrylamino)-3-methyl-N-thiazol-2-yl-benzamide:

LC/MS (m/z) 332 (MH+); RT=2.44 (method A).

2d: 3-Bromo-4-(3,3-dimethyl-butyrylamino)-N-thiazol-2-yl-benzamide:

LC/MS (m/z) 397 (MH+); RT=2.85 (method A).

2e: 4-Isobutyrylamino-2-methoxy-N-thiazol-2-yl-benzamide:

LC/MS (m/z) 320 (MH+); RT=2.20 (method A).

2f: 3-Fluoro-4-(3-methyl-butyrylamino)-N-thiazol-2-yl-benzamide:

LC/MS (m/z) 322 (MH+); RT=2.41 (method A).

2g: 4-(3,3-Dimethyl-butyrylamino)-3-fluoro-N-thiazol-2-yl-benzamide:

LC/MS (m/z) 336 (MH+); RT=2.74 (method A).

2h: 4-(3,3-Dimethyl-butyrylamino)-3,5-difluoro-N-thiazol-2-yl-benzamide:

LC/MS (m/z) 354 (MH+); RT=2.5 (method A).

2i: 5-Chloro-4-(cyclopentanecarbonyl-amino)-2-methoxy-N-thiazol-2-yl-benzamide:

LC/MS (m/z) 381 (MH+); RT=3.09 (method A).

2j: 5-Chloro-2-methoxy-4-(2-methyl-benzoylamino)-N-thiazol-2-yl-benzamide:

LC/MS (m/z) 403 (MH+); RT=3.15 (method A).

2k: 3-Chloro-4-(2-cyclopentyl-acetylamino)-N-thiazol-2-yl-benzamide:

LC/MS (m/z) 365 (MH+); RT=2.92 (method A).

2l: 3,5-Dichloro-4-(3,3-dimethyl-butyrylamino)-N-thiazol-2-yl-benzamide:

The reaction mixture was heated in a microwave oven at 120° C. for 2.5 h.

LC/MS (m/z) 387 (MH+); RT=2.76 (method A).

General Procedure for the Preparation of Compounds with Formula I

Examples

3a: Amino-acetic acid 2-[(E/Z)-4-(3,3-dimethyl-butyrylamino)-benzoylimino]-thiazol-3-ylmethyl ester hydrochloride:

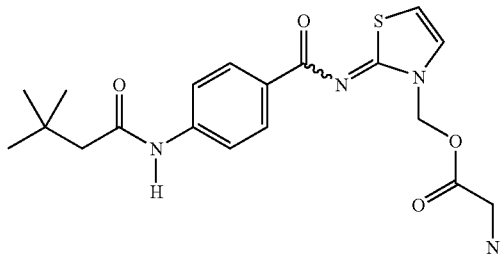

NaH (3 mmol) was weighed into a flamedried flask in an argon atmosphere and suspended in DMF (12 mL). 4-(3,3-Dimethyl-butyrylamino)-N-thiazol-2-yl-benzamide (2,5 mmol) was added and the mixture stirred for 1 h at room temperature. tert-Butylcarbonylamino-glycine choromethylene ester (2,5 mmol) was added and the reaction mixture was stirred at room temperature over night. The solvent was evaporated and the product was purified by flash chromatography on silica gel using 20%-50% EtOAc in heptane as eluent.

Yield: 59%

1H NMR (D$_6$-DMSO): 1.02 (s, 9H); 1.33 (s, 9H); 2.22 (s, 2H); 3.73 (d, 2H); 6.24 (s, 2H); 7.00 (d, 1H); 7.27 (t, 1H); 7.57 (d, 1H); 7.69 (d, 2H); 8.12 (d, 2H); 10.03 (s, 1H).

tert-Butoxycarbonylamino-acetic acid {[4-(3,3-dimethyl-butyrylamino)-benzoyl]-thiazol-2-yl-amino}-methyl ester was suspended in ether saturated with HCl gas and allowed to react for 15 min. The solvent was removed and the product was dried in vacuo.

Yield: 100%

1H NMR (D$_6$-DMSO): 1.02 (s, 9H); 2.22 (s, 2H); 3.91 (m, 2H); 6.35 (s, 2H); 7.03 (d, 1H); 7.60 (d, 1H); 7.71 (d, 2H); 8.14 (d, 2H); 8.32 (m, 2H); 10.11 (s, 1H).

The following were prepared analogously:

3b: (S)-2-Amino-3-methyl-butyric acid 2-[(E/Z)-3-chloro-4-(2-cyclopentyl-acetylamino)-benzoylimino]-thiazol-3-ylmethyl ester hydrochloride:

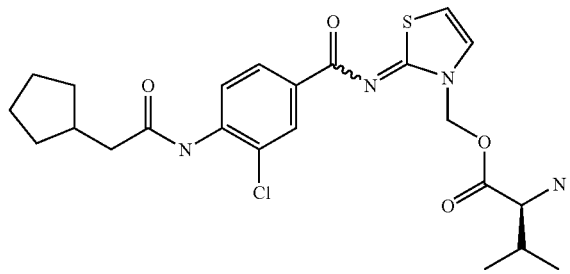

Prepared from 3-chloro-4-(2-cyclopentyl-acetylamino-N-thiazol-2-yl-benzamide and (S)-2-tert-butoxycarbonylamino-3-methyl-butyric acid chloromethyl ester followed by deprotection.

LC/MS (m/z) 493 (MH$^+$); RT=2.13 (method B).

3c: 2-(S)-Amino-3-methyl-butyric acid 2-[(E/Z)-3-bromo-4-(3,3-dimethyl-butyrylamino)-benzoylimino]-thiazol-3-ylmethyl ester hydrochloride:

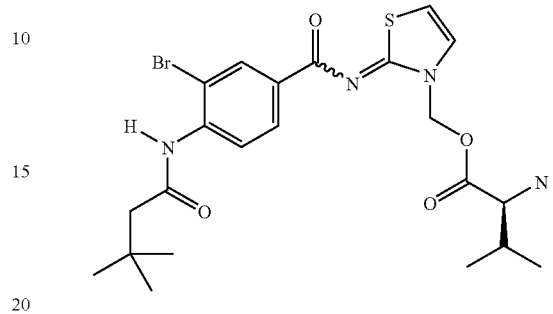

Prepared from 3-bromo-4-(3,3-dimethyl-butyrylamino)-N-thiazol-2-yl-benzamide and (S)-2-tert-butoxycarbonylamino-3-methyl-butyric acid chloromethyl ester followed by deprotection.

LC/MS (m/z) 525 (MH$^+$); RT=2.1 (method A).

3d: 2-(S)-Amino-3-methyl-butyric acid 2-[(E/Z)-4-(3,3-dimethyl-butyrylamino)-3,5-difluoro-benzoylimino]-thiazol-3-ylmethyl ester hydrochloride:

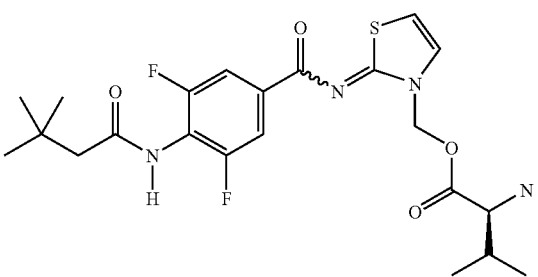

Prepared from 4-(3,3-dimethyl-butyrylamino)-3,5-difluoro-N-thiazol-2-yl-benzamide and (S)-2-tert-butoxycarbonylamino-3-methyl-butyric acid chloromethyl ester followed by deprotection.

LC/MS (m/z) 483 (MH$^+$); RT=1.92 (method A).

3e: 2-(S)-Amino-3-methyl-butyric acid 2-[(E/Z)-4-(3,3-dimethyl-butyrylamino)-3-fluoro-benzoylimino]-thiazol-3-ylmethyl ester hydrochloride:

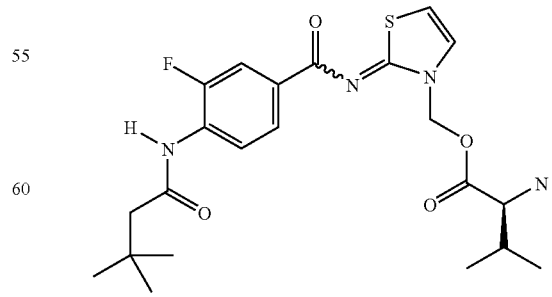

Prepared from 4-(3,3-dimethyl-butyrylamino)-3-fluoro-N-thiazol-2-yl-benzamide and (S)-2-tert-butoxycarbony lamino-3-methyl-butyric acid chloromethyl ester followed by deprotection.
LC/MS (m/z) 465 (MH⁺); RT=2.14 (method A).

3f: 2-(S)-Amino-3-methyl-butyric acid 2-[(E/Z)-4-(3,3-dimethyl-butyrylamino)-3-methyl-benzoylimino]-thiazol-3-yl-methyl ester hydrochloride:

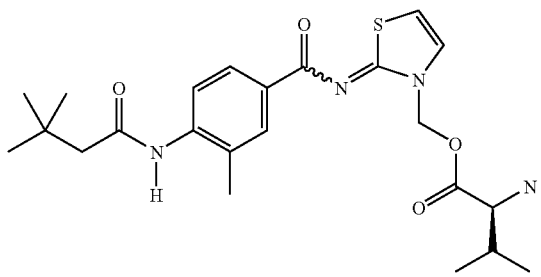

Prepared from 4-(3,3-dimethyl-butyrylamino)-3-methyl-N-thiazol-2-yl-benzamide and (S)-2-tert-butoxycarbonylamino-3-methyl-butyric acid chloromethyl ester followed by deprotection.
LC/MS (m/z) 461 (MH⁺); RT=1.88 (method A).

3g: 2-(S)-Amino-3-methyl-butyric acid 2-[(E/Z)-4-(3,3-dimethyl-butyrylamino)-benzoylimino]-thiazol-3-ylmethyl ester hydrochloride:

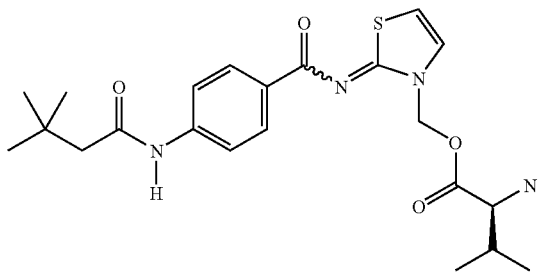

Prepared from 4-(3,3-dimethyl-butyrylamino)-3-methyl-N-thiazol-2-yl-benzamide and (S)-2-tert-butoxycarbonylamino-3-methyl-butyric acid chloromethyl ester followed by deprotection.
LC/MS (m/z) 447 (MH⁺); RT=1.83 (method A).

3h: 2-(S)-Amino-3-methyl-butyric acid 2-[(E/Z)-5-chloro-2-methoxy-4-(2-methyl-benzoylamino)-benzoylimino]-thiazol-3-ylmethyl ester hydrochloride:

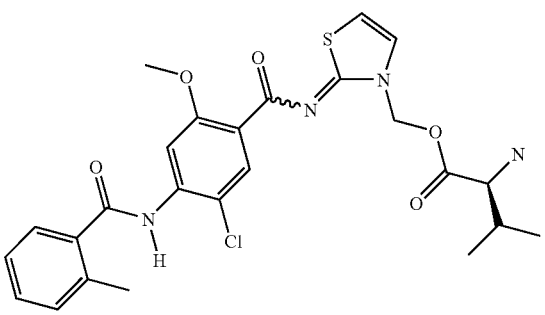

Prepared from 5-chloro-2-methoxy-4-(2-methyl-benzoylamino)-N-thiazol-2-yl-benzamide and (S)-2-tert-butoxycarbonylamino-3-methyl-butyric acid chloromethyl ester followed by deprotection. LC/MS (m/z) 531 (MH⁺); RT=2.2 (method A).

3i: (S)-2-Amino-3-methyl-butyric acid 2-[(E/Z)-5-chloro-4-(cyclopentanecarbonyl-amino)-2-methoxy-benzoylimino]-thiazol-3-ylmethyl ester hydrochloride:

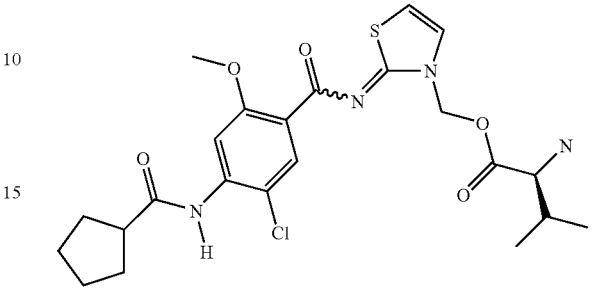

Prepared from 5-chloro-4-(cyclopentanecarbonyl-amino)-2-methoxy-N-thiazol-2-yl-benzamide and (S)-2-tert-butoxycarbonylamino-3-methyl-butyric acid chloromethyl ester followed by deprotection. LC/MS (m/z) 509 (MH⁺); RT=2.09 (method A).

3j: (2S,3S)-2-Amino-3-methyl-pentanoic acid 2-[(E/Z)-3-chloro-4-(2-cyclopentyl-acetylamino)-benzoylimino]-thiazol-3-ylmethyl ester hydrochloride:

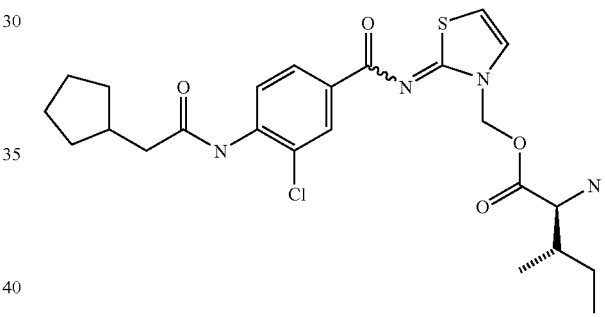

Prepared from 3-chloro-4-(2-cyclopentyl-acetylamino)-N-thiazol-2-yl-benzamide and (2S,3S)-2-tert-Butoxycarbonylamino-3-methyl-pentanoic acid chloromethyl ester followed by deprotection.
LC/MS (m/z) 507 (MH⁺); RT=2.17 (method B).

3k: (2S,3S)-2-Amino-3-methyl-pentanoic acid 2-[(E/Z)-3-bromo-4-(3,3-dimethyl-butyrylamino)-benzoylimino]-thiazol-3-ylmethyl ester hydrochloride:

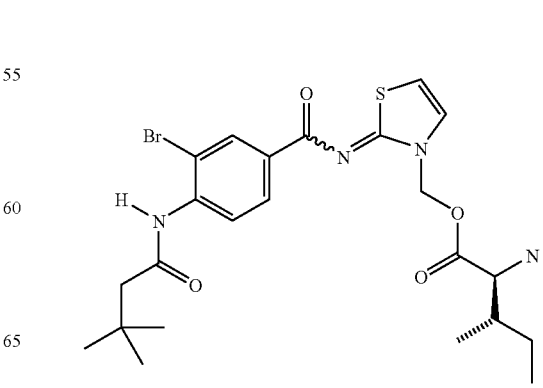

Prepared from 3-bromo-4-(3,3-dimethyl-butyrylamino)-N-thiazol-2-yl-benzamide and (2S,3S)-2-tert-Butoxycarbonylamino-3-methyl-pentanoic acid chloromethyl ester followed by deprotection.

LC/MS (m/z) 539 (MH+); RT=2.16 (method A).

3l: (2S,3S)-2-Amino-3-methyl-pentanoic acid 2-[(E/Z)-3-fluoro-4-(3-methyl-butyrylamino)-benzoylimino]-thiazol-3-ylmethyl ester hydrochloride:

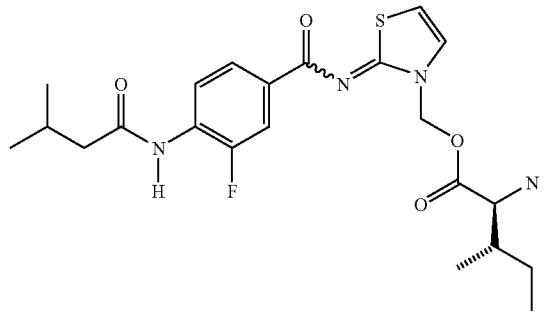

Prepared from 3-fluoro-4-(3-methyl-butyrylamino)-N-thiazol-2-yl-benzamide and (2S,3S)-2-tert-Butoxycarbonylamino-3-methyl-pentanoic acid chloromethyl ester followed by deprotection.

LC/MS (m/z) 465 (MH+); RT=1.88 (method B).

3m: (2S,3S)-2-Amino-3-methyl-pentanoic acid 2-[(E/Z)-4-(3,3-dimethyl-butyrylamino)-3,5-difluoro-benzoylimino]-thiazol-3-ylmethyl ester hydrochloride:

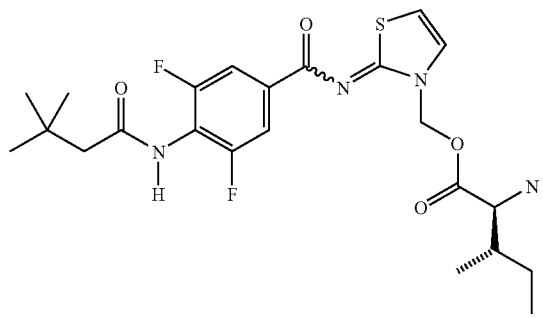

Prepared from 4-(3,3-dimethyl-butyrylamino)-3,5-difluoro-N-thiazol-2-yl-benzamide and (2S,3S)-2-tert-Butoxycarbonylamino-3-methyl-pentanoic acid chloromethyl ester followed by deprotection.

LC/MS (m/z) 497 (MH+); RT=1.98 (method A).

3n: (2S, 3S)-2-Amino-3-methyl-pentanoic acid 2-[(E/Z)-4-(3,3-dimethyl-butyrylamino)-3-fluoro-benzoylimino]-thiazol-3-ylmethyl ester hydrochloride:

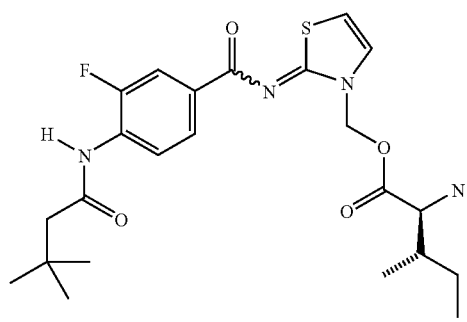

Prepared from 4-(3,3-dimethyl-butyrylamino)-3-fluoro-N-thiazol-2-yl-benzamide and (2S,3S)-2-tert-Butoxycarbonylamino-3-methyl-pentanoic acid chloromethyl ester followed by deprotection.

LC/MS (m/z) 479 (MH+); RT=1.97 (method B).

3o: (2S, 3S)-2-Amino-3-methyl-pentanoic acid 2-[(E/Z)-4-(3,3-dimethyl-butyrylamino)-benzoylimino]-thiazol-3-ylmethyl ester hydrochloride:

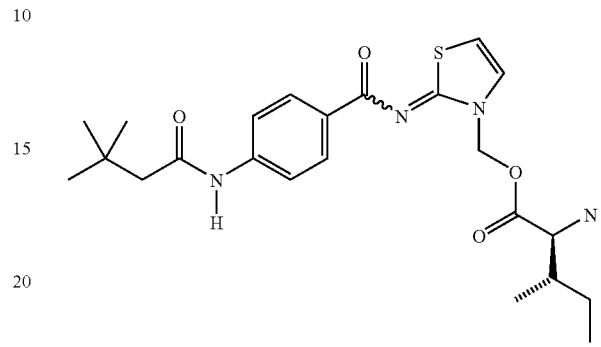

Prepared from 4-(3,3-dimethyl-butyrylamino)-3-methyl-N-thiazol-2-yl-benzamide and (2S,3S)-2-tert-Butoxycarbonylamino-3-methyl-pentanoic acid chloromethyl ester followed by deprotection.

LC/MS (m/z) 461 (MH+); RT=1.91 (method A).

3p: (2S, 3S)-2-Amino-3-methyl-pentanoic acid 2-[(E/Z)-4-(3,3-dimethyl-butyrylamino)-3-methoxy-benzoylimino]-thiazol-3-ylmethyl ester hydrochloride:

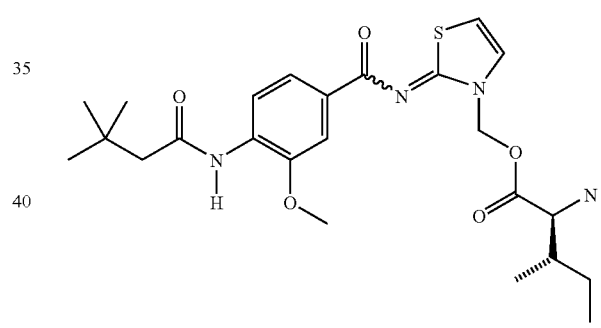

Prepared from 4-(3,3-dimethyl-butyrylamino)-3-methoxy-N-thiazol-2-yl-benzamide and (2S,3S)-2-tert-Butoxycarbonylamino-3-methyl-pentanoic acid chloromethyl ester followed by deprotection.

LC/MS (m/z) 491 (MH+); RT=2.05 (method A).

3q: (S)-Pyrrolidine-2-carboxylic acid 2-[(E/Z)-3-bromo-4-(3,3-dimethyl-butyrylamino)-benzoylimino]-thiazol-3-ylmethyl ester hydrochloride:

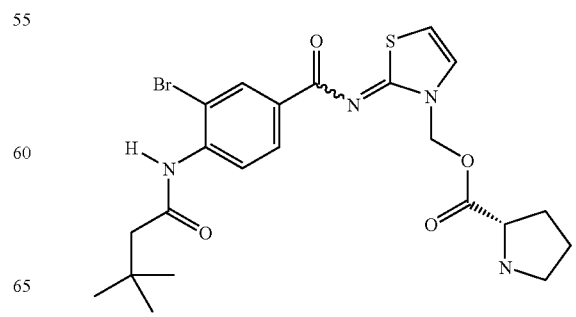

Prepared from 3-bromo-4-(3,3-dimethyl-butyrylamino)-N-thiazol-2-yl-benzamide and (S)-pyrrolidine-1,2-dicarboxylic acid 1-tert-butyl ester 2-chloromethyl ester followed by deprotection.

LC/MS (m/z) 525 (MH$^+$); RT=2.02 (method A).

3r: (S)-Pyrrolidine-2-carboxylic acid 2-[(E/Z)-3-chloro-4-(2-cyclopentyl-acetylamino)-benzoylimino]-thiazol-3-ylmethyl ester hydrochloride:

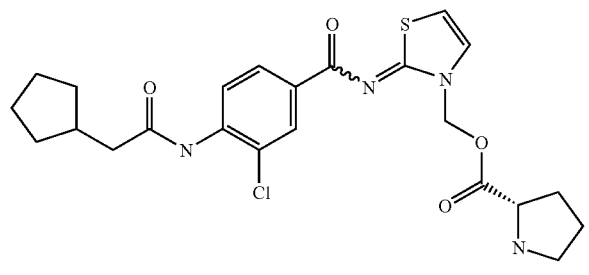

Prepared from 3-chloro4-(2-cyclopentyl-acetylamino)-N-thiazol-2-yl-benzamide and (S)-pyrrolidine-1,2-dicarboxylic acid 1-tert-butyl ester 2-chloromethyl ester followed by deprotection.

LC/MS (m/z) 491 (MH$^+$); RT=2.04 (method B).

3s: (S)-Pyrrolidine-2-carboxylic acid 2-[(E/Z)-3fluoro-4-(3-methyl-butyrylamino)benzoylimino]-thiazol-3-ylmethyl ester hydrochloride:

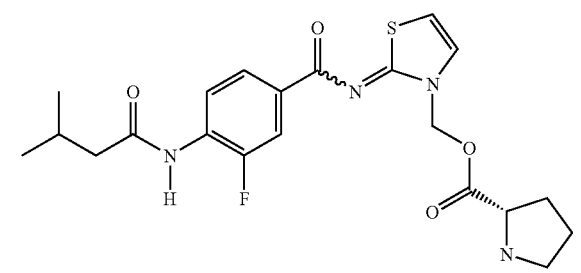

Prepared from 3-fluoro-4-(3-methyl-butyrylamino)-N-thiazol-2-yl-benzamide and (S)-pyrrolidine-1,2-dicarboxylic acid 1-tert-butyl ester 2-chloromethyl ester followed by deprotection.

LC/MS (m/z) 449 (MH$^+$); RT=1.93 (method A).

3t: (S)-Pyrrolidine-2-carboxylic acid 2-[(E/Z)-4-(3,3-dimethyl-butyrylamino)-3-fluoro-benzoylimino]-thiazol-3-ylmethyl ester hydrochloride:

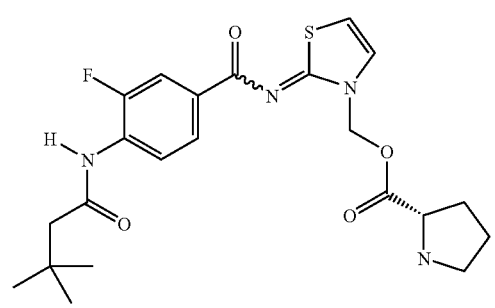

Prepared from 4-(3,3-dimethyl-butyrylamino)-3-fluoro-N-thiazol-2-yl-benzamide and (S)-pyrrolidine-1,2-dicarboxylic acid 1-tert-butyl ester 2-chloromethyl ester followed by deprotection.

LC/MS (m/z) 463 (MH$^+$); RT=1.86 (method B).

3u: (S)-Pyrrolidine-2-carboxylic acid 2-[(E/Z)-4-(3, 3-dimethyl-butyrylamino)-3-methoxy-benzoylimino]-thiazol-3-ylmethyl ester hydrochloride:

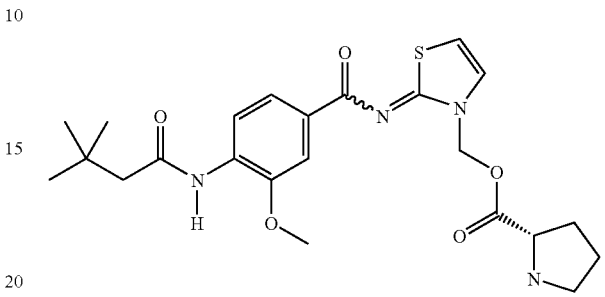

Prepared from 4-(3,3-dimethyl-butyrylamino)-3-methoxy-N-thiazol-2-yl-benzamide and (S)-pyrrolidine-1,2-dicarboxylic acid 1-tert-butyl ester 2-chloromethyl ester followed by deprotection.

LC/MS (m/z) 475 (MH$^+$); RT=1.9 (method B).

3v: (S)-Pyrrolidine-2-carboxylic acid 2-[(E/Z)-4-(3,3-dimethyl-butyrylamino)-3-methyl-benzoylimino]-thiazol-3-ylmethyl ester hydrochloride:

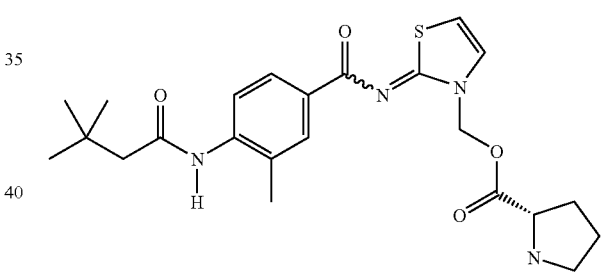

Prepared from 4-(3,3-dimethyl-butyrylamino)-3-methyl-N-thiazol-2-yl-benzamide and (S)-pyrrolidine-1,2-dicarboxylic acid 1-tert-butyl ester 2-chloromethyl ester followed by deprotection.

LC/MS (m/z) 459 (MH$^+$); RT=1.81 (method A).

3w: 2-Amino-2-methyl-propionic acid 2-[(E/Z)-4-(3,3-dimethyl-butyrylamino)-3-methoxy-benzoylimino]-thiazol-3-ylmethyl ester hydrochloride:

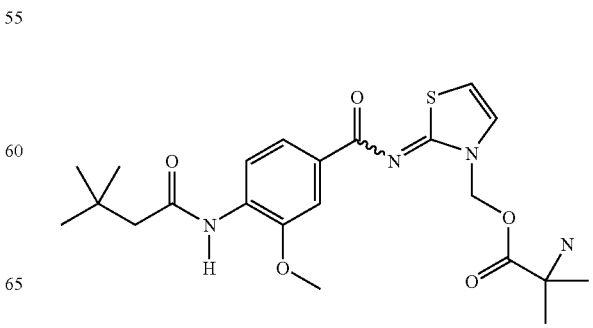

Prepared from 4-(3,3-dimethyl-butyrylamino)-3-methoxy-N-thiazol-2-yl-benzamide and 2-tert-butoxycarbonylamino-2-methyl-propionic acid chloromethyl ester followed by deprotection.

LC/MS (m/z) 463 (MH$^+$); RT=1.92 (method A).

3x: 2-Amino-2-methyl-propionic acid 2-[(E/Z)-3-fluoro-4-(3-methyl-butyrylamino)-benzoylimino]-thiazol-3-ylmethyl ester hydrochloride:

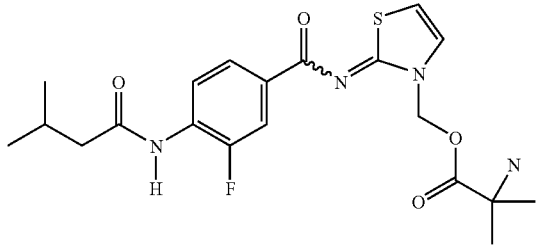

Prepared from 3-fluoro-4-(3-methyl-butyrylamino)-N-thiazol-2-yl-benzamide and 2-tert-butoxycarbonylamino-2-methyl-propionic acid chloromethyl ester followed by deprotection.

LC/MS (m/z) 437 (MH$^+$); RT=1.76 (method A).

3y: 2-Amino-2-methyl-propionic acid 2-[(E/Z)-4-(3,3-dimethyl-butyrylamino)-3fluoro-benzoylimino]-thiazol-3-ylmethyl ester hydrochloride:

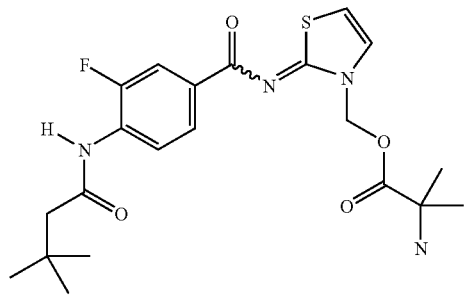

Prepared from 4-(3,3-dimethyl-butyrylamino)-3-fluoro-N-thiazol-2-yl-benzamide and 2-tert-butoxycarbonylamino-2-methyl-propionic acid chloromethyl ester followed by deprotection.

LC/MS (m/z) 451 (MH$^+$); RT=1.84 (method B).

3z: Piperidine-4-carboxylic acid 2-[(E/Z)-4-isobutyrylamino-2-methoxy-benzoylimino]-thiazol-3-ylmethyl ester hydrochloride:

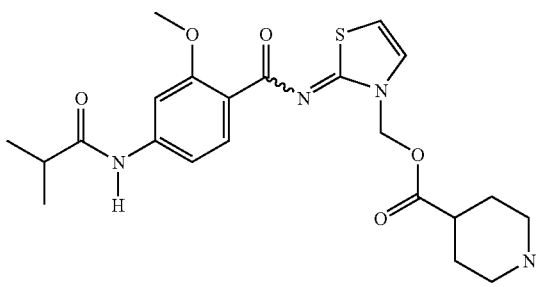

Prepared from 4-isobutyrylamino-2-methoxy-N-thiazol-2-yl-benzamide and piperidine-1,4-dicarboxylic acid 1-tert-butyl ester 4-chloromethyl ester followed by deprotection.

LC/MS (m/z) 461 (MH$^+$); RT=1.91 (method A).

4a: Piperidine-4-carboxylic acid 2-[(E/Z)-3-bromo-4-(3,3-dimethyl-butyrylamino)-benzoylimino]-thiazol-3-ylmethyl ester hydrochloride:

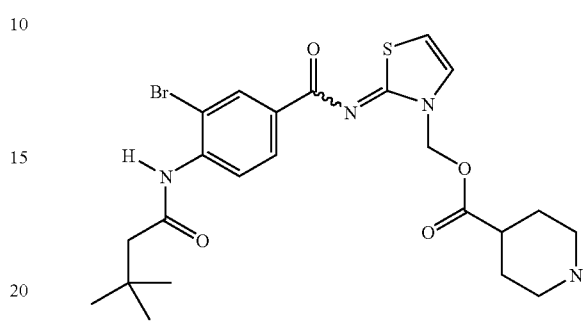

Prepared from 3-bromo-4-(3,3-dimethyl-butyrylamino)-N-thiazol-2-yl-benzamide and piperidine-1,4-dicarboxylic acid 1-tert-butyl ester 4-chloromethyl ester followed by deprotection.

LC/MS (m/z) 537 (MH$^+$); RT=2.06 (method A).

4b: Piperidine-4-carboxylic acid 2-[(E/Z)-3-chloro-4-(3-ethyl-hexanoylamino-benzoylimino]-thiazol-3-ylmethyl ester hydrochloride:

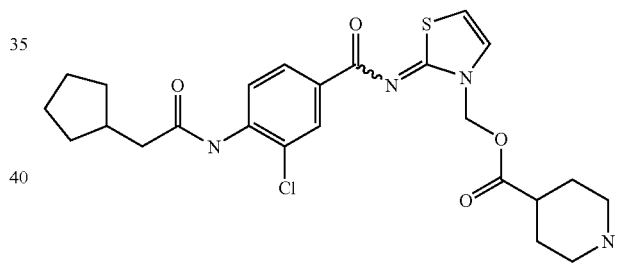

Prepared from 3-chloro-4-(2-cyclopentyl-acetylamino)-N-thiazol-2-yl-benzamide and piperidine-1,4-dicarboxylic acid 1-tert-butyl ester 4-chloromethyl ester followed by deprotection.

LC/MS (m/z) 505 (MH$^+$); RT=2.04 (method B).

4c: Piperidine-4-carboxylic acid 2-[(E/Z)-3-fluoro-4-(3-methyl-butyrylamino)-benzoylimino]-thiazol-3-ylmethyl ester hydrochloride:

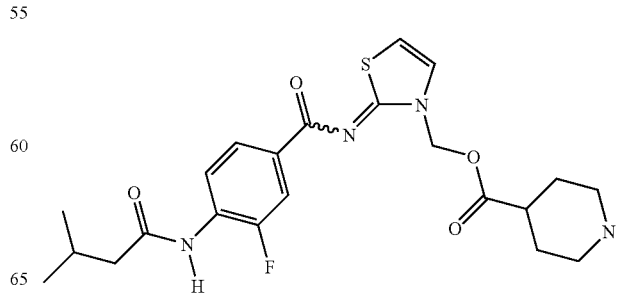

Prepared from 3-fluoro-4-(3-methyl-butyrylamino)-N-thiazol-2-yl-benzamide and piperidine-1,4-dicarboxylic acid 1-tert-butyl ester 4-chloromethyl ester followed by deprotection.

LC/MS (m/z) 463 (MH⁺); RT=1.81 (method A).

4d: Piperidine-4-carboxylic acid 2-[(E/Z)-4-(3,3-dimethyl-butyrylamino)-3-methyl-benzoylimino]-thiazol-3-ylmethyl ester hydrochloride:

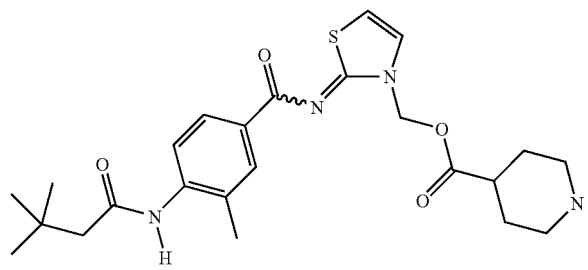

Prepared from 4-(3,3-dimethyl-butyrylamino)-3-methyl-N-thiazol-2-yl-benzamide and piperidine-1,4-dicarboxylic acid 1-tert-butyl ester 4-chloromethyl ester followed by deprotection.

LC/MS (m/z) 473 (MH⁺); RT=1.77 (method A).

4e: Piperidine-4-carboxylic acid 2-[(E/Z)-5-chloro-2-methoxy-4-(2-methyl-benzoylamino)-benzoylimino]-thiazol-3-ylmethyl ester hydrochloride:

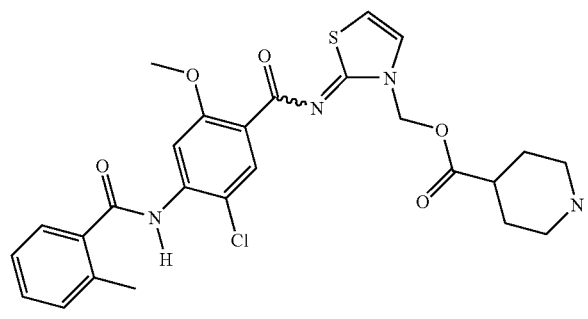

Prepared from 5-chloro-2-methoxy-4-(2-methyl-benzoylamino)-N-thiazol-2-yl-benzamide and piperidine-1,4-dicarboxylic acid 1-tert-butyl ester 4-chloromethyl ester followed by deprotection.

LC/MS (m/z) 543 (MH⁺); RT=1.89 (method A).

4f: Piperidine-4-carboxylic acid 2-[(E/Z)-5-chloro-4-(cyclopentanecarbonyl-amino)-2-methoxy-benzoylimino]-thiazol-3-ylmethyl ester hydrochloride:

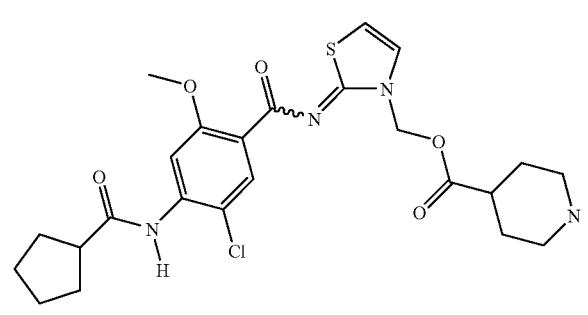

Prepared from 5-chloro-4-(cyclopentanecarbonyl-amino)-2-methoxy-N-thiazol-2-yl-benzamide and piperidine-1,4-dicarboxylic acid 1-tert-butyl ester 4-chloromethyl ester followed by deprotection.

LC/MS (m/z) 521 (MH⁺); RT=1.76 (method B).

4g: 3-Amino-propionic acid 2-[(E/Z)-4-(3,3-dimethyl-butyrylamino)-3,5-difluoro-benzoylimino]-thiazol-3-ylmethyl ester hydrochloride:

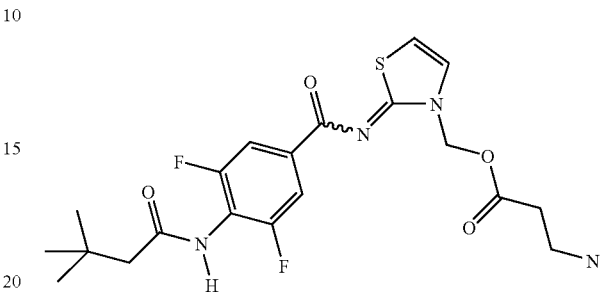

Prepared from 4-(3,3-dimethyl-butyrylamino)-3,5-difluoro-N-thiazol-2-yl-benzamide and 3-tert-butoxycarbonylamino-propionic acid chloromethyl ester followed by deprotection.

1H NMR (D₆-DMSO): 1.05 (s, 9H); 2.25 (s, 2H); 2.75 (t, 2H); 3.03 (m, 2H); 6.31 (s, 2H); 7.14 (d, 1H); 7.70 (d, 1H); 7.86 (d, 2H); 9.76 (s, 1H).

4h: (S)-2-Methylamino-propionic acid 2-[(E/Z)-4-(3,3-dimethyl-butyrylamino)-3,5-difluoro-enzoylimino]-thiazol-3-ylmethyl ester hydrochloride:

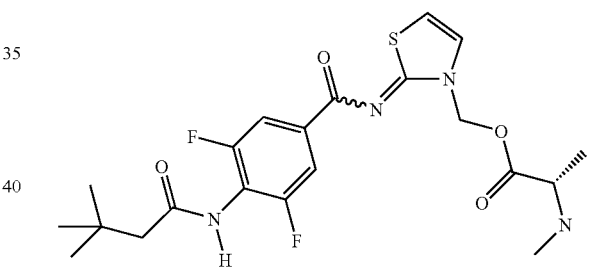

Prepared from 4-(3,3-dimethyl-butyrylamino)-3,5-difluoro-N-thiazol-2-yl-benzamide and (S)-2-tert-butoxycarbonyl-methyl-amino-propionic acid chloromethyl ester followed by deprotection.

1H NMR (D₆-DMSO): 1.05 (s, 9H); 1.42 (d, 3H); 2.26 (s, 2H); 2.54 (m, 3H); 4.20 (m, 1H); 6.42 (m, 2H); 7.16 (d, 1H); 7.76 (d, 1H); 7.86 (d, 2H); 9.83 (br s, 1H).

4i: (R,S)-2-Amino-2,3-dimethyl-butyric acid 2-[(E/Z)-4-(3,3-dimethyl-butyrylamino)-3,5-difluoro-benzoylimino]-thiazol-3-ylmethyl ester hydrochloride:

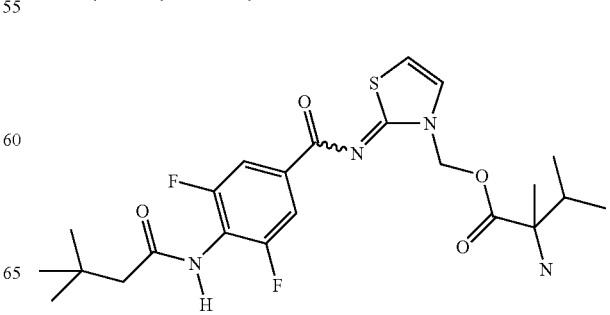

Prepared from 4-(3,3-dimethyl-butyrylamino)-3,5-difluoro-N-thiazol-2-yl-benzamide and (R,S)-2-tert-butoxycarbonylamino-2,3-dimethyl-butyric acid chloromethyl ester followed by deprotection.

1H NMR (D$_6$-DMSO): 0.83 (d, 3H); 0.85 (d, 3H); 1.05 (s, 9H); 1.43 (s, 3H); 2.04 (m, 1H); 2.25 (s, 2H); 6.42 (dd, 2H); 7.16 (d, 1H); 7.75 (d, 1H); 7.86 (d, 2H); 8.63 (br, 3H); 9.79 (s, 1H).

4j: (2S,3S)-2-Dimethylamino-3-methyl-pentanoic acid 2-[(E/Z)-4-(3,3-dimethyl-butyrylamino)-3,5-difluoro-benzoylimino]-thiazol-3-ylmethyl ester:

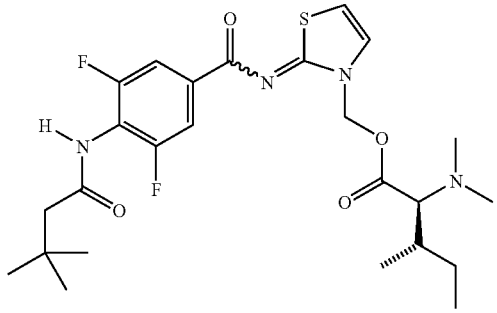

(2S, 3S)-2-Amino-3-methyl-pentanoic acid 2-[(E/Z)-4-(3,3-dimethyl-butyrylamino)-3,5-difluoro-benzoylimino]-thiazol-3-ylmethyl ester hydrochloride (3.3 mmol) was dissolved in MeOH (100 mL), and sodium cyanoborohydride (7.4 mmol) was added followed by formaldehyde (37% in water, 8.3 mmol). Stirred at room temperature for h. The reaction mixture was evaporated and the residue partitioned between ethyl acetate and water. The organic phase was washed with water, dried over MgSO$_4$, filtered and evaporated. The crude product was purified by flash chromatography on silica usig 40% EtOAc in heptane as eluent.

Yield: 26%

1H NMR (D$_6$-DMSO): 0.73 (d, 3H); 0.77 (t, 3H); 1.05 (s, 9H); 1.28 (m, 1H); 1.57 (m, 1H); 1.75 (m, 1H); 2.13 (s, 6H); 2.25 (s, 2H); 4.30 (d, 1H); 6.32 (m, 2H); 7.13 (d, 1H); 7.75 (d, 1H); 7.86 (d, 2H); 7.92 (s, 1H).

4k: Phosphoric acid mono-{2-[(E/Z)-4-(3,3-dimethyl-butyrylamino)-3,5-difluoro-benzoylimino]-thiazol-3-ylmethyl}ester:

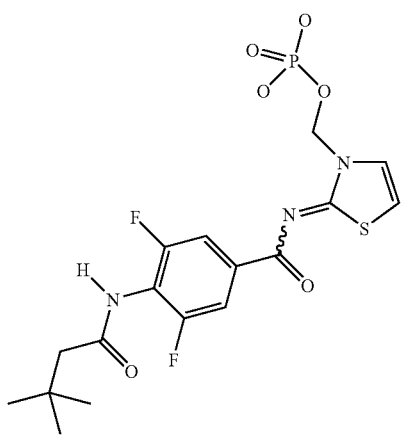

Prepared from 4-(3,3-dimethyl-butyrylamino)-3,5-difluoro-N-thiazol-2-yl-benzamide and phosphoric acid di-tert-butyl ester chloromethyl ester followed by deprotection using 5 eq. trifluoroacetic acid in dichloromethane at ambient temperature over night, followed by lyophilisation.

LC/MS (m/z) 464 (MH$^+$); RT=1.91 (method A).

4l: Phosphoric acid mono-{2-[(E/Z)-4-(3,3-dimethyl-butyrylamino)-benzoylimino]-thiazol-3-ylmethyl}ester

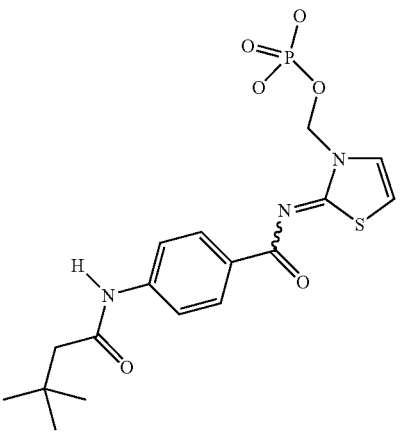

Prepared from 4-(3,3-dimethyl-butyrylamino)-N-thiazol-2-yl-benzamide and phosphoric acid di-tert-butyl ester chloromethyl ester, followed by deprotection using 5 eq. trifluoroacetic acid in dichloromethane, at ambient temperature over night, followed by lyophilisation.

1H NMR (D$_6$-DMSO): 1.03 (s, 9H); 2.23 (s, 2H); 5.99 (d, 2H); 7.02 (d, 1H); 7.55 (d, 1H); 7.70 (d, 2H); 8.18 (d, 2H); 10.05 (s, 1H).

4m: Phosphoric acid mono-{2-[(E/Z)-4-(3,3-dimethyl-butyrylamino)-3-fluoro-benzoylimino]-thiazol-3-ylmethyl}ester

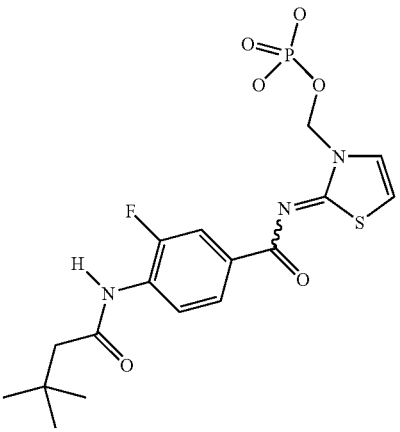

Prepared from 4-(3,3-dimethyl-butyrylamino)-3-fluoro-N-thiazol-2-yl-benzamide and phosphoric acid di-tert-butyl ester chloromethyl ester, followed by deprotection using 5 eq. trifluoroacetic acid in dichloromethane, at ambient temperature over night, followed by lyophilisation.

1H NMR (D$_6$-DMSO): 1.04 (s, 9H); 2.32 (s, 2H); 6.01 (d, 2H); 7.06 (d, 1H); 7.59 (d, 1H); 7.98-8.10 (3H); 9.74 (s, 1H).

4n: Phosphoric acid mono-{2-[(E/Z)-3,5-dichloro-4-(3,3-dimethyl-butyrylamino)-benzoylimino]-thiazol-3-ylmethyl}ester

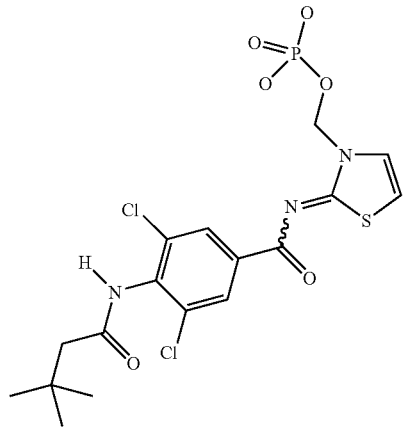

Prepared from 4-(3,3-dimethyl-butyrylamino)-3,5-chloro-N-thiazol-2-yl-benzamide and phosphoric acid di-tert-butyl ester chloromethyl ester, followed by deprotection using 5 eq. trifluoroacetic acid in dichloromethane, at ambient temperature over night, followed by lyophilisation.

1H NMR (D$_6$-DMSO): 1.08 (s, 9H); 2.26 (s, 2H); 5.92 (d, 2H); 7.04 (d, 1H); 7.69 (d, 1H); 8.18 (s, 2H); 9.81 (s, 1H).

4o: (R,S)-Carbonic acid 2,3-dihydroxy-propyl ester 2-[(E/Z)-4-(3,3-dimethyl-butyrylamino)-3,5-difluoro-benzoylimino]-thiazol-3-ylmethyl ester:

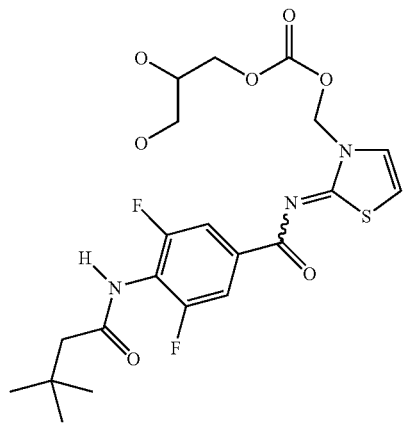

Prepared from 4-(3,3-dimethyl-butyrylamino)-3,5-difluoro-N-thiazol-2-yl-benzamide and (R,S)-carbonic acid chloromethyl ester 2,2-dimethyl-[1,3]dioxolan-4-ylmethyl ester, followed by deprotection by gently shaking an ethanol/water (1:1) solution of the protected product in the presence of acidic ion-exchange resin DOWEX 50 WX2-100 at 30° C. for 3 h. The mixture was filtered and evaporated to give the product.

1H NMR (D$_6$-DMSO): 1.05 (s, 9H); 2.26 (s, 2H); 3.28-3.32 (m, 1H); 3.33-3.38 (m, 1H); 3.62-3.70 (m, 1H); 4.02-4.09 (m, 1H); 4.18-4.24 (m, 1H); 6.30 (s, 2H); 7.13 (d, 1H); 7.69 (d, 1H); 7.88 (m, 2H); 9.76 (s, 1H).

4p: 4-(3,3-Dimethyl-butyrylamino)-3,5-difluoro-N-{3-[(1S,3S,4S,5R)-3,4,5-trihydroxy-6-((R)-hydroxymethyl)-tetrahydro-pyran-2-yloxymethyl]-3H-thiazol-2-ylidene}-benzamide

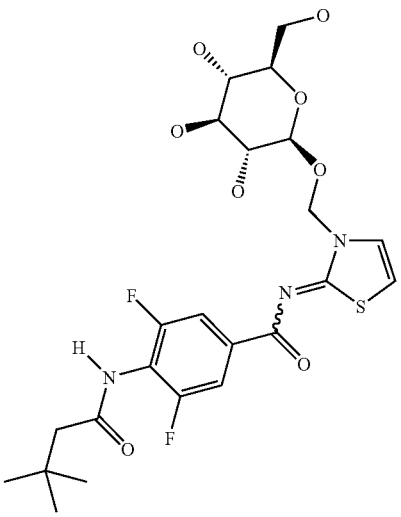

N-(3-Chloromethyl-3H-thiazol-2-ylidene)-4-(3,3-dimethyl-butyrylamino)-3,5-difluoro-benzamide (1.2 mmol) and acetic acid (2R,3R,4S,5R,6R)-4,5-diacetoxy-6-acetoxymethyl-2-hydroxy-tetrahydro-pyran-3-yl ester (1.5 mmol) was combined in a flamedried flask in an Argon atmosphere and suspended in dry dichloromethane (15 mL). The mixture was cooled to −60° C. and AgOTf (2.9 mmol) was added. The reaction mixture was allowed to slowly heat to −20° C. and stirred for 1 h, then the mixture was slowly heated to room temperature and stirred overnight. The crude reaction mixture was cooled to 0° C. and NaHCO3 (aq., sat.) (15 mL) was added with stirring. The mixture was filtered and water and ethyl acetate was added. The organic phase was separated and washed with NaHCO3 (aq., sat.) until the washing were basic, dried on MgSO$_4$, filtered and evaporated.

The crude product was purified by flash chromatography using a gradient of 1-10% MeOH in 1:1 ethylacetate/heptane as eluent.

Yield: 11%

The product (0.14 mmol) was deprotected by dissolution in MeOH (3 mL) and addition of NaOMe (0.56 mmol). The reaction mixture was stirred overnight at room temperature. Acidic DOWEX 50W ion exchange resin was added and the mixture was stirred until the reaction mixture was neutralized. The resin was removed by filtration and the product was recovered by evaporation of the solvent. The isolated product was of the beta configuration.

Yield: 98%

1H NMR (D$_6$-DMSO): 1.05 (s, 9H); 2.26 (s, 2H); 2.97-3.18 (4H); 3.49 (m, 1H); 3.62 (m, 1H); 4.51 (d, 1H); 5.74 (d, 1H); 6.07 (d, 1H); 7.10 (d, 1H); 7.71 (d, 1H); 7.85 (d, 2H); 9.84 (s, 1H).

4q: 4-(3,3-Dimethyl-butyrylamino)-3,5-difluoro-N-[3-((2R, 3R,4S,5S,6R)-3,4,5-trihydroxy-6-hydroxymethyl-tetrahydro-pyran-2-yl)-3H-thiazol-2-ylidene]-benzamide

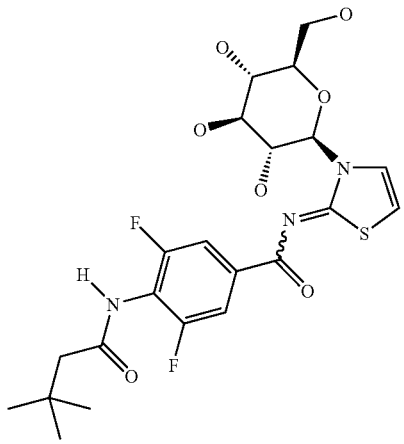

4-(3,3-dimethyl-butyrylamino)-3,5-difluoro-N-thiazol-2-yl-benzamide (1.4 mmol) was suspended in hexamethyldisilazane (8.1 mmol) and chlorotrimethylsilane (1.7 mmol) in a sealed container, and stirred at 160° C. for 14 h. The excess silylating agent was then removed under reduced pressure, and the crude was used directly without further purification.

The crude silylation product and acetic acid (2R,3R,4S,5R, 6R)-4,5-diacetoxy-6-acetoxymethyl-2-hydroxy-tetrahydropyran-3-yl ester (1.4 mmol) were combined in a flamedried flask in an Argon atmosphere and dichloromethane (4 mL) was added. The mixture was cooled on ice, and trimethylsilyltriflate (1.7 mmol) was added. The reaction mixture was allowed to warm to room temperature, and stirred overnight. The crude mixture was diluted with dichloromethane (2 mL) and cold NaHCO3 (aq., sat.) was added. Ethyl acetate was added to separate the phases and the organic layer was washed with water, dried over $MgSO_4$, filtered and evaporated. The product was purified by flash chromatography on silica using 7% MeOH in 7:3 heptane/ethyl acetate as eluent.

Yield: 15%

The purified product was deprotected by suspension in MeOH (3 mL) and addition of NaOMe (4 eq.). The mixture was stirred overnight at room temperature, then acidic ion exchange resin DOWEX 50W was added to neutralize the reaction mixture. When neutral the resin was filtered off and the product was recovered by evaporation of the solvent.

Yield: 98%

1H NMR ($D_6$-DMSO): 1.04 (s, 9H); 2.25 (s, 2H); 3.27 (m, 1H); 3.45-3.57 (2H); 3.64-3.75 (3H); 6.05 (d, 1H); 7.10 (d, 1H); 7.71 (d, 1H); 7.86 (d, 2H); 9.76 (s, 1H).

List of Reagents

Reagents used for the preparation of compounds 1a-4q:

| Name | CAS no. | Supplier | Catalog no. |
| --- | --- | --- | --- |
| 2-aminothiazole | 96-50-4 | AVOCADO | 12026 |
| 4-Nitro benzoic acid chloride | 122-04-3 | AVOCADO | A12543-0B |
| 4-Nitro-3-methyl benzoic acid | 3113-71-1 | ALDRICH | M6,060-0 |
| 4-Nitro-3-methoxy benzoic acid | 5081-36-7 | ALDRICH | 18,430-6 |
| 4-Nitro-3-fluoro benzoic acid | 403-21-4 | SYNCHEM-INC | SH-10091 |
| 4-Amino-3-chloro benzoic acid methyl ester | 84228-44-4 | AVOCADO | 22519 |
| 4-Amino benzoic acid | 150-13-0 | AVOCADO | A12673-0B |
| 4-Amino-5-chloro-2-methoxy benzoic acid | 7206-70-4 | ALDRICH | 34,087-1 |
| 4-Amino-3,5-dichloro benzoic acid | 56187-37-2 | ALDRICH | 54,598-8 |
| 4-Amino-3,5-difluoro benzoic acid | — | BUTTPARK | 35/03-09 |
| 3,3-Dimethyl-butyric acid chloride | 7065-46-5 | ALDRICH | B8,880-2 |
| 3-Methylbutyryl chloride | 108-12-3 | ALDRICH | 15,742-2 |
| Cyclopentanecarbonyl chloride | 4524-93-0 | ALDRICH | 32,831-6 |
| 2-Methylpropanoyl chloride | 79-30-1 | AVOCADO | B24472.22 |
| 2-Methyl benzoyl chloride | 933-88-0 | ALDRICH | 12,201-7 |
| N-tert-Butyloxycarbonyl L-valine | 13734-41-3 | ALDRICH | 35,972-6 |
| N-tert-Butyloxycarbonyl L-isoleucine | 13139-16-7 | ALDRICH | 35,965-3 |
| N-tert-Butyloxycarbonyl L-proline | 15761-39-4 | ALDRICH | 13,457-0 |
| N-tert-Butyloxycarbonyl glycine | 4530-20-5 | ALDRICH | 13,453-8 |
| N-tert-Butyloxycarbonyl Piperidine-4-carboxylic acid | 84358-13-4 | APOLLO | OR5410 |
| N-tert-Butyloxycarbonyl-2-amino isobutyric acid | 30992-29-1 | NOVABIOCHEM | 0412-0203 |
| N-tert-Butyloxycarbonyl beta-Alanine | 3303-84-2 | NOVABIOCHEM | 04-12-0100 |
| N-methyl-N-tert-Butyloxycarbonyl Alanine | 16948-16-6 | FLUKA | 15549 |
| N-tert-Butyloxycarbonyl α-methyl valine | 139938-00-4 | BACHEM | A-4145.0005 |
| Phosphorous acid di-tert-butyl ester | 13086-84-5 | JOHNSON-MATTHEY | X00455G0025 |
| Glycerol dimethylketal | 100-79-8 | ALDRICH | 12,269-6 |
| Chloromethyl chloroformate | 22128-62-7 | JOHNSON-MATTHEY | X09527G0010 |
| Caesium carbonate | 534-17-8 | ALDRICH | 44,190-2 |
| Tetrabutylammonium hydrogensulphate | 32503-27-8 | | |
| Chlorosulphonic acid | 7790-94-5 | ALDRICH | 18,630-9 |
| Bromochloromethane | 74-97-5 | ACROS | 15913-0010 |

-continued

| Name | CAS no. | Supplier | Catalog no. |
|---|---|---|---|
| Chloroiodomethane | 593-71-5 | ALFA | 31155 |
| Tetramethylammonium hydroxide | 75-59-2 | ALDRICH | 33,163-5 |
| Sodium hydride | 7646-69-7 | ALDRICH | 45,291-2 |
| N-bromo succinimide | 128-08-5 | ALDRICH | B8,125-5 |
| 1-Hydroxy benzotriazole | 2592-95-2 | FLUKA | 54802 |
| 1-(3-Dimethylaminopropyl)-3-ethyl-carbodiimide hydrochloride | 25952-53-8 | ALDRICH | 16, 146-2 |
| Formaldehyde (37% aq.) | 50-00-0 | ALDRICH | 25,254-9 |
| Sodium cyano borohydride | 25895-60-7 | ALDRICH | 29,681-3 |
| Thionyl chloride | 7719-09-7 | ACROS | 16949-0010 |
| Oxalyl chloride | 79-37-8 | ALDRICH | 32,042-0 |
| Trifluoroacetic acid | 76-05-1 | ALDRICH | T6,220-0 |
| 1,2-Dimethoxyethane | 110-71-4 | ALDRICH | 30,743-2 |
| Hexamethyldisilazane | 999-97-3 | ALDRICH | 37,921-2 |
| Chloromethylsilane | 75-77-4 | ALDRICH | C7,285-4 |
| Trimethylsilyl trifluoromethane-sulfonate | 27607-77-8 | ALDRICH | 22,564-9 |
| Silver trifluoromethanesulfonate | 2923-28-6 | ALDRICH | 17,643-5 |
| 2,3,4,6-Tetra-O-acetyl-D-gluco-pyranose | 10343-06-3 | TORONTO | T280000 |
| DOWEX 50 W | 12612-37-2 | ALDRICH | 27,881-5 |

Example 3

Pharmacological Testing

The ability of a compound with formula I to release a compound with formula V under physiological conditions can, e.g., be assessed by administering a compound with formula I to a mammal and subsequently analysing the blood of said mammal for the corresponding compound with formula V.

In the following a general method is exemplified of assessing the conversion under physiological conditions of a compound with formula I, to release a compound with formula V, i.e. verification of the conversion of pro-drug to parent compound in vivo in rats.

Assessing the Conversion of Pro-Drug to Parent Compound in Vivo in Rats

Dosing: 2 mg/kg of the pro-drug dissolved in saline or 10% HP-beta cyclodextrin is administered by oral gavage to cannulated SD rats.

Blood sampling: Blood samples is drawn at the following time points, relative to time of dosing: pre-dose, 5 min, 20 min, 50 min, 2 h, 4 h, 7 h, 11 h, 15 h, and 20 h.

Sample preparation: At the end of the experiment, the blood samples is centrifuged at 15000×g for 10 min, and the plasma subsequently transferred to fresh vials and frozen at −80° C. until quantitative analysis.

Bio analysis: The blood samples are analysed for pro-drug and parent compound. Analysis of plasma samples may be performed by liquid chromatography separation /tandem mass spectrometry (LC-MS/MS).

The compounds with formula V may be characterised in vitro according to the following methods:

$A_{2A}$ Efficacy Assays

Cloning of the human cDNA encoding the $A_{2a}$ receptor cDNA was obtained by random primed reverse transcription of human fetal brain RNA (Clonetech). A subsequent polymerase chain reaction (PCR) was performed using the cDNA as template and the oligonucleotides TTTACGCGTG-GCCATGCCCATCATGGGCTCCTC (SEQ ID NO:1) and TTTCTAGAATCAGGACACTCCTGCTCCATC (SEQ ID NO:2) as primers for the amplification. The amplification was performed using Pfu polymerase (Stratagene, in accordance with the manufacturer's recommendation) with an annealing temperature of 54° C. The reaction mixture was analyzed by an agarose gel electrophoresis and a band of 1.2 kb was excised and the DNA eluted. The eluted DNA was digested with the restriction enzymes MluI and XbaI and ligated into a vector, pCIneo, cut with the same enzymes. DNA was isolated and sequenced. CHO cells were transfected with the pCIneo clone expressing the $A_{2a}$ receptor and cells with stable integration of the plasmids were isolated after 2-3 weeks growth in the presence of either 5 mg/ml or 10 mg/ml G418.

CHO cells transfected with $A_{2A}$ receptors as described above were grown in F12 nutrient mixture (kaighs modification, Life technologies) with 10% FCS, 1% glutamin and 1% penicillin/streptomycin and 1 mg/mL G418.

24 h prior to assay performance, 10000 cells/well were seeded in costar 96-well plates in media without G418 to 60-80% confluence. The cells were stimulated with NECA (00-9498, final concentration 75 nM) corresponding to about 80% agonist efficacy.

The cell media was removed and the cells washed 3 times in 37° C. pre-equilibrated PBS and incubated (on shaker) with 10 μL of a suspension of acceptor beads and 10 μL of a solution of test compound or standard compound (0-10 μM) in darkness for 30 min at 25° C. before addition of 30 μl of a suspension of donor beads and further incubation 60-120 min in darkness. The plates were analysed according to manufacturers instruction (Alpha screen, Perkin Elmer (Pachard Bioscience)).

The acceptor beads were suspended in a stimulation buffer (5 mM HEPES, 0.1% BSA in Hanks balanced salt pH 7.4 w/o phenol red (Gibco). The donor beads were suspended in a lysis buffer (the stimulation buffer with 0,3% Tween 20 and biotinylated cAMP) according to manufacturers instruction (Alpha screen, Perkin Elmer (Pachard Biosciense)).

The data were fitted with non-linear regression, and $IC_{50}$ and $K_i$ values were calculated from the equations:

$$IC_{50} = ([I]/(100/(100 - \%INH)))/(1 + ([ag]/EC_{50}))$$

and $$K_i = IC_{50}/(1 - [ag]/EC_{50}),$$

where [I] is the inhibitor concentration, [ag] is the assay agonist concentration and $EC_{50}$ is the agonist concentration required for half maximal effect.

$A_{2A}$ Binding Assay

Membrane Preparations for $A_{2A}$ Binding Analysis:

Expression in Insect Cells

The human $A_{2a}$ encoding DNA were excised from the pCIneo constructs by MluI and XbaI and subcloned into the pFASTBAC2 vector cut with XbaI and BssHII. The inserts were recombined into the baculo vector using the Bac-to-Bac® system (Invitrogen). The generation and isolation of baculo virus was performed as described by the distributor (Invitrogen). High Five cells (Invitrogen) was grown at 27° C. in suspension to a density of $1*10^6$ and infected with a MOI of 0.5. The cells are harvested 72 h post infection and membranes prepared.

High five cells expressing $A_{2A}$ receptors were homogenized in 50 mM tris-buffer pH 7.4 in an ultra Turrax homogenisator. The membranes were diluted to a concentration of 0.6 mg/ml and 2U Adenosine deaminase (Roche)/ml membrane suspension was added. The solution was preincubated 30 min at 37° C. before use.

$A_{2A}$ Binding Analysis

Binding assay was performed in 96 well flat bottom plate and initiated by mixing 10.6 µg protein/well with solutions of standard compounds or test compounds (final concentrations 0-10 µM) and 1 nM final concentration of $^3$H-ZM241385 (R1036 from Tocris). All test compounds were diluted in 50 nM trisbuffer from DMSO-stocks (2 mM or 10 mM). The reactions (final volume=200 µL) were incubated for 30 min at 25° C. and washed on Unifilter-GF/B with water. The filters were dried 20 min (37° C.) before addition of 35 µl Microscient-0 or Optiphase supermix and counting in a Trilux counter for 1 min.

The data were fitted with non-linear regression, and $IC_{50}$ and $K_i$ values were calculated from the equations:

$IC_{50}=([I]/(100/(100-\%INH))/(1+([L]/K_D)$ and $K_i=IC_{50}/(1-[L]/K_D)$, where [I] is the inhibitor concentration, and [L] and $K_D$ are concentration and dissociation equilibrium constant of the radiotracer, respectively.

The exemplified compounds with structure V are $A_{2A}$ receptors antagonists having a human $A_{2A}$ binding affinity ($K_i$) of 200 nM or less.

The invention claimed is:

1. A compound with formula I $$A\text{-}B\text{-}Z;\qquad\qquad I$$

wherein Z is formula II

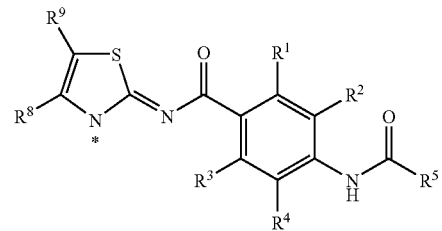

II wherein $R^1$-$R^4$ are independently selected from hydrogen, halogen, $C_{1-6}$-alkyl and $C_{1-6}$-alkoxy;
$R^5$ is $C_{1-8}$-alkyl;
$R^8$ and $R^9$ are both hydrogen;
* indicates the atom attached to B;
A is selected from the group consisting of mono-, di-, and tri-phosphates, or esters or salts thereof; and
B is formula III

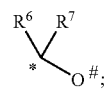

III wherein $R^6$ and $R^7$ are independently selected from hydrogen and methyl and * indicates the atom attached to Z, and # indicates the atom attached to A;

or a pharmaceutically acceptable addition salt thereof.

2. The compound of claim 1, wherein $R^5$ is selected from the group consisting of $C_{3-8}$-alkyl, $C_{4-8}$-alkyl branched at the β-position.

3. The compound of claim 2, wherein $R^5$ is a neopentyl or isobutyl.

4. The compound of claim 1, wherein $R^1$ and $R^3$ are independently selected from the group consisting of hydrogen and methoxy.

5. The compound of claim 4, wherein $R^1$ and $R^3$ are both methoxy and $R^2$ and $R^4$ are both hydrogen.

6. The compound of claim 1, wherein $R^2$ and $R^4$ are independently selected from the group consisting of hydrogen, halogen, and methyl.

7. The compound of claim 6, wherein $R^2$ and $R^4$ are independently selected from fluoro, chloro, and methyl, and wherein $R^1$ and $R^3$ are both hydrogen.

8. The compound of claim 1, wherein said compound is selected from the group consisting of:
$R^1=R^2=R^3=R^4=R^8=R^9=H$ and $R^5$=neopentyl;
$R^1=R^3=R^4=R^8=R^9=H$, $R^2$=Br and $R^5$=neopentyl;
$R^1=R^3=R^8=R^9=H$, $R^2R^4=F$ and $R^5$=neopentyl;
$R^1=R^3=R^4=R^8=R^9H$, $R^2=F$ and $R^5$=neopentyl;
$R^1=R^3=R^4=R^8=R^9=H$, $R^2$=methyl and $R^5$=neopentyl;
$R^1=R^3=R^4=R^8=R^9=H$, $R^2$=methoxy and $R^5$=neopentyl;
$R^2=R^3=R^4=R^8=R^9=H$, $R^1$=methoxy and $R^5$=isopropyl;
$R^1=R^3=R^4=R^8=R^9=H$, $R^2$=F and $R^5$=isobutyl; and
$R^1=R^3=R^8=R^9=H$, $R^2=R^4$=Cl and $R^5$=neopentyl.

9. The compound of claim 1, wherein A is selected from mono-phosphates, and mono-phosphates mono esters; or salts thereof.

10. The compound of claim 1, wherein both $R^6$ and $R^7$ are hydrogen, or $R^6$ is hydrogen and $R^7$ is methyl.

11. The compound of claim 1, wherein both $R^6$ and $R^7$ are hydrogen.

12. The compound of claim 1, wherein A-B- of formula I is a phosphoric acid monomethylenyl ester.

13. A pharmaceutical composition comprising the compound of claim 1 and a pharmaceutically acceptable carrier.

14. The compound of claim 1, wherein A and B link to form a monophosphate having the formula $$\underset{*}{\overset{R^6\ R^7}{\diagdown}}\mathrm{O-\underset{\underset{O}{|}}{\overset{\overset{O}{\|}}{P}}-O;}$$

or an ester or salt thereof.

15. The compound of claim 14, wherein the compound is selected from the group consisting of:

Phosphoric acid mono-{2-[(E/Z)-4-(3,3-dimethyl-butyrylamino)-3,5-difluoro-benzoylimino]-thiazol-3-ylmethyl}ester;

Phosphoric acid mono-{2-[(E/Z)-4-(3,3-dimethyl-butyrylamino)-benzoylimino]-thiazol-3-ylmethyl}ester;

Phosphoric acid mono-{2-[(E/Z)-4-(3,3-dimethyl-butyrylamino)-3-fluoro-benzoylimino]-thiazol-3-ylmethyl}ester; and Phosphoric acid mono-{2-[(E/Z)-3,5-dichloro-4-(3,3-dimethyl-butyrylamino)-benzoylimino]-thiazol-3-ylmethyl}ester; or a pharmaceutically acceptable addition salt thereof.

16. A pharmaceutical composition comprising the compound of claim 15 and a pharmaceutically acceptable carrier.

17. A method for symptomatic relief in a subject suffering from Parkinson's Disease comprising administering to the subject a therapeutically effective amount of the compound of claim 1.

18. A method for symptomatic relief in a subject suffering from Parkinson's Disease comprising administering to the subject a therapeutically effective amount of the compound of claim 14.

19. A method for symptomatic relief in a subject suffering from Parkinson's Disease comprising administering to the subject a therapeutically effective amount of the compound of claim 2.

20. A method for symptomatic relief in a subject suffering from Parkinson's Disease comprising administering to the subject a therapeutically effective amount of the compound of claim 3.

21. A method for symptomatic relief in a subject suffering from Parkinson's Disease comprising administering to the subject a therapeutically effective amount of the compound of claim 7.

22. A method for symptomatic relief in a subject suffering from Parkinson's Disease comprising administering to the subject a therapeutically effective amount of the compound of claim 8.

23. A method for symptomatic relief in a subject suffering from Parkinson's Disease comprising administering to the subject a therapeutical effective amount of the compound of claim 15.

* * * * *

```
                         SEQUENCE LISTING

<160> NUMBER OF SEQ ID NOS: 2

<210> SEQ ID NO 1
<211> LENGTH: 33
<212> TYPE: DNA
<213> ORGANISM: Homo sapiens

<400> SEQUENCE: 1
tttacgcgtg gccatgccca tcatgggctc ctc                             33

<210> SEQ ID NO 2
<211> LENGTH: 30
<212> TYPE: DNA
<213> ORGANISM: Homo sapiens

<400> SEQUENCE: 2
tttctagaat caggacactc ctgctccatc                                 30
```